US006849722B2

(12) United States Patent
Warner et al.

(10) Patent No.: US 6,849,722 B2
(45) Date of Patent: Feb. 1, 2005

(54) POLYMERIZED OLIGOPEPTIDE-SURFACTANT CHIRAL MICELLES

(75) Inventors: Isiah M. Warner, Baton Rouge, LA (US); Eugene J. Billiot, Baton Rouge, LA (US); Shahab A. Shamsi, Atlanta, GA (US); Stefan J. Thibodeaux, Des Allemands, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 138 days.

(21) Appl. No.: 09/876,304

(22) Filed: Jun. 7, 2001

(65) Prior Publication Data

US 2001/0051703 A1 Dec. 13, 2001

Related U.S. Application Data

(62) Division of application No. 09/296,351, filed on Apr. 22, 1999, now Pat. No. 6,270,640.
(60) Provisional application No. 60/126,431, filed on Apr. 29, 1998.

(51) Int. Cl.$^7$ .............................................. A61K 38/00
(52) U.S. Cl. ...................... 530/415; 204/451; 204/455
(58) Field of Search ......................... 530/415; 204/451; 514/44; 210/635; 525/426

(56) References Cited

U.S. PATENT DOCUMENTS

| 5,770,084 A | 6/1998 | Warner et al. ............... 210/635 |
| 6,013,738 A | * 1/2000 | Daly et al. ................... 525/426 |

FOREIGN PATENT DOCUMENTS

| JP | 4149205 | 5/1992 |
| JP | 4149206 | 5/1992 |

OTHER PUBLICATIONS

Billiot et al. Chiral separatoins using dipeptide polymerized surfactants: effect of amino acid order. Anal. Chem. (Apr. 1, 1998) 70: 1375–1381 [As cited also in IDS].*
Shamsi et al. Improved chiral separations using a polymerized dipeptide anionic chiral surfactant in electrokinetic chromatography: separations of basic, acidic, and neutral racemates. Anal. Chem. (Aug. 1, 1997) 69: 2980–2987 [As cited also in IDS].*
Armstrong, D., "Optical Isomer Separation by Liquid Chromatography," Anal. Chem., vol. 59, pp. 84A–91A (1987).
Armstrong, D. et al., "Enrichment of Enantiomers and Other Isomers with Aqueous Liquid Membranes Containing Cyclodextrin Carriers," Anal. Chem., vol. 59, pp. 2237–2241 (1987).
Baczuk, R. J. et al., "Liquid Chromatographic Resolution of Racemic β–3,4–Dihydroxyphenylalanine," J. Chromatog., vol. 60, pp. 351–361 (1971).
Billiot, E. et al., "Effect of Amino Acid Order on Chiral Separations in Dipeptide Surfactants," Abstract No. 1010 from Pittcon '98 (New Orleans, LA, Mar. 1–5, 1998).
Billiot, E. et at., "Chiral Separations Using Dipeptide Polymerized Surfactants: Effect of Amino Acid Orderr," Anal. Chem. vol. 70, 1375–1381 (1998).
Dobashi, Akira, et al., "Enantiomeric Separation with Sodium Dodecanoyl–L–amino Acidate Micelles and Poly–(sodium (10–undecenoyl)–L–valinate) by Electrokinetic Chromatography," Anal. Chem. vol. 67, 3011–3017 (1995).
Fendler, J. et al., "Polymerized Surfactant Aggregates: Characterization and Utilization," Acc. Chem. Res., vol. 17, pp. 3–8 (1984).
Gassmann, E. et al., "Electrokinetic Separation of Chiral Compounds," Science, vol. 230, pp. 813–814 (1985).
Ishihama, Y. et al., "Enantiomeric Separation by Micellar Electrokinetic Chromatography Using Saponins," J. Liq. Chromatog., vol. 16, pp. 933–944 (1993).
Kuhn, R. et al., "Chiral Separation by Capillary Electrophoresis," Chromatographia, vol. 34, pp. 505–512 (1992).
Larrabee, C. et al., "Radiation–Induced Polymerization of Sodium 10–Undecenoate in Aqueous Micelle Solutions," J. Poly. Sci.: Poly. Lett. Ed., vol. 17, pp. 749–751 (1979).
Leydet, A. et al., "Polyanion Inhibitors of Human Immunodeficiency Virus and Other Viruses, Part 2.," J. Med. Chem. vol. 39, 1626–1634 (1996).
Novotny, M. et al., "Chiral Separation through Capillary Electromigration Methods," Anal. Chem., vol. 66, pp. 646A–655A (1994).
Otsuka, Koji et al., "Enantiomeric Resolution by Micellar Electrokinetic Chromatography with Chiral Surfactants," J. Chromatog., vol. 515, pp. 221–226 (1990).

(List continued on next page.)

Primary Examiner—Christopher R. Tate
Assistant Examiner—Maury Audet
(74) Attorney, Agent, or Firm—John H. Runnels

(57) ABSTRACT

Chiral separations can be enhanced through the use of polymerized dipeptide-surfactant or oligopeptide-surfactant chiral micelles. Because polymerized micelles eliminate much of the complex dynamic behavior associated with conventional micelles, polymerized chiral micelles have stronger chiral recognition properties than do otherwise-identical, "conventional" or non-polymerized chiral micelles. Recovery of chiral ligands from polymerized chiral micelles is often easier, as the chiral ligands may typically be recovered by simple extraction with an appropriate organic solvent. By contrast, recovering the solute from a conventional, non-polymerized micellar medium by extraction with an organic solvent frequently results in the formation of troublesome emulsion systems. Polymerized chiral micelle systems are therefore beneficial in both preparative-scale and process-scale separations. Polymerized chiral micelles have no critical micelle concentration, allowing lower concentrations to be used in micellar electrokinetic capillary chromatography, which in turn reduces the otherwise deleterious heat that can be generated. Many polymerized dipeptide-surfactant or oligopeptide-surfactant chiral micelles have superior separation properties as compared to polymerized amino acid-surfactant chiral micelles.

10 Claims, 6 Drawing Sheets

OTHER PUBLICATIONS

Paleos, C. et al., "Comparative Studies between Monomeric and Polymeric Sodium 10–Undecenoate Micelles," J. Phys. Chem., vol. 87, pp. 251–254 (1983).

Palmer, C. et al., "A Monomolecular Pseudostationary Phase for Micellar Electrokinetic Capillary Chromatography," J. High Res. Chromatog., vol. 15, pp. 756–762 (1992).

Shamsi, S. et al., "Comparison of Single Amino Acids versus Dipeptide Polymerized Surfactants for Chiral Separations in Electrokinetic Chromatography," Abstract No. 1008 from Pittcon '98 (New Orleans, LA, Mar. 1–5, 1998).

Shamsi, S. et al., "Improved Chiral Separations Using a Polymerized Dipeptide Anionic Chiral Surfactant in Electrokinetic Chromatography: Separations of Basic, Acidic, and Neutral Racemates," *Anal. Chem.* vol. 69, 2980–2987 (1997).

Tabor, Dennis G. et al., "Some Factors in Solute Partitioning between Water and Micelles or Polymeric Micelle Analogues," Chromatog., vol. 20, pp. 73–80 (1989).

Taguchi et al., "Immobilized Bilayer Stationary Phases in Gas Chromatography," J. Chem. Soc., Chem. Commun., pp. 364–365 (1986).

Terabe, S. et al., "Chiral Separation by Electrokinetic Chromatography with Bile SaltMicelles," J. Chromatog., vol. 480, pp. 403–411 (1989).

Terabe, S. et al., "Electrokinetic Chromatography with Micellar Solution and Open–Tubular Capillary," Anal. Chem., vol. 57, pp. 834–841 (1985).

Terabe, S. et al., "Electrokinetic Separations with Micellar Solutions and Open–Tubular Capillaries," Anal. Chem., vol. 56, pp. 111–113 (1984).

Terabe, S. et al., "Ion–Exchange Electrokinetic Chromatography with Polymer Ions for the Separation of Isomeric Ions Having Identical Electrophoretic Mobilities," Anal. Chem., vol. 62, pp. 650–652 (1990).

Terabe, S. et al., "Separation of Enantiomers by Capillary Electrophoretic Techniques," J. Chromatog. A, vol. 666, pp. 295–319 (1994).

Wang, J.; Warner, I. M., "Combined Polymerized chiral Micelle and γ–cyclodextrin for chiral separation in capillary electrophoresis," *J. Chromatog.* 711, 297–304(1995).

Wang, J. et al., "Chiral Separations Using Micellar Electrokinetic Capillary Chromatography and a Polymerized Chiral Micelle," *Anal. Chem.* vol. 66, 3773–3776 (1994).

Ward, T. "Chiral Media for Capillary Electrophoresis," *Anal. Chem.*, vol. 66, pp. 632A–640A (1994).

* cited by examiner

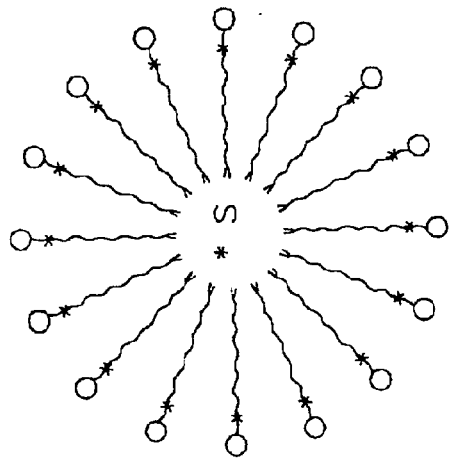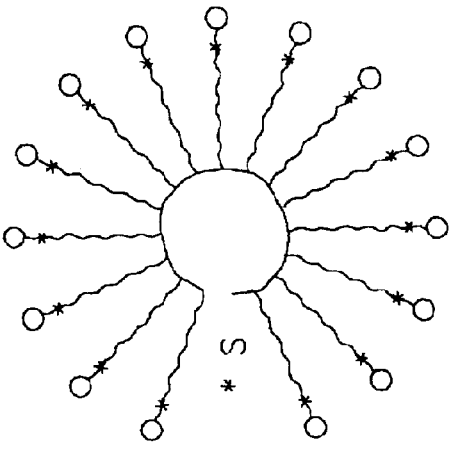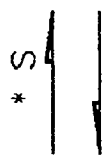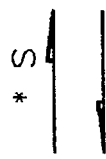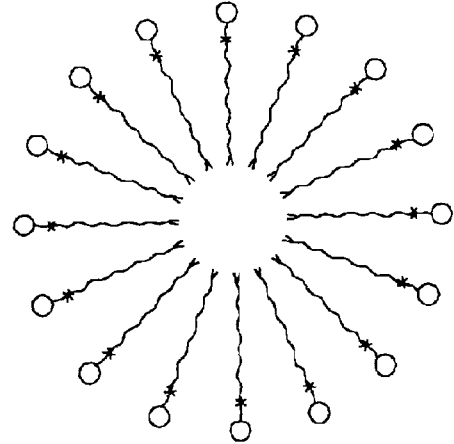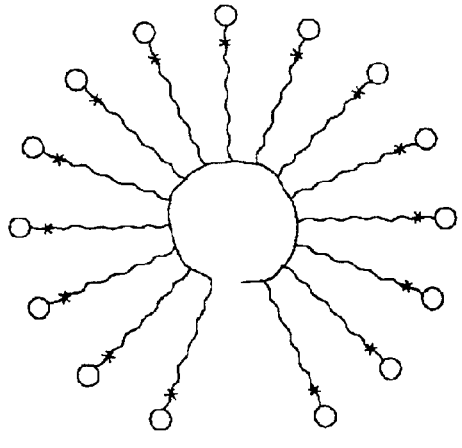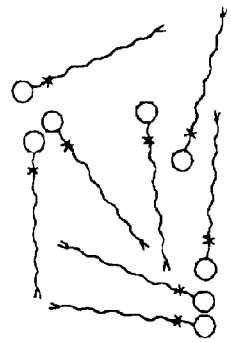
FIGURE 1(a)
FIGURE 1(b)

R=$C_8H_{17}$

X=1=poly [sodium N-undecylenyl-L-valine] (poly [L-SUV])

X=2=poly [sodium N-undecylenyl-L-valine-valine] (poly [L-SUVV])

POLYMERIZED OLIGOPEPTIDE-SURFACTANT CHIRAL MICELLES

This is a divisional of application Ser. No. 09/296,351, filed Apr. 22, 1999, now U.S. Pat. No. 6,270,640; which claims the benefit of the Apr. 29, 1998 filing date of provisional application 60/126,431 under 35 U.S.C. §119(e).

The development of this invention was partially funded by the Government through a grant from the National Institutes of Health, number GM-39844. The Government has certain rights in this invention.

This invention pertains to methods and compositions useful in chiral separations of enantiomeric mixtures, particularly to the use of polymerized chiral micelles in such separations.

Chiral Separations

The separation of enantiomeric mixtures into individual optical isomers is one of the most challenging problems in analytical chemistry, reflecting practical considerations important in many areas of science, particularly the pharmaceutical and agricultural industries.

For example, the pharmaceutically active site of many drugs is "chiral," meaning that the active site is not identical to a mirror image of the site. However, many pharmaceutical formulations marketed today are racemic mixtures of the desired compound and its "mirror image." One optical form (or enantiomer) of a racemic mixture may be medicinally useful, while the other optical form may be inert or even harmful, as has been reported to be the case for thalidomide.

Chiral drugs are now extensively evaluated prior to large scale manufacturing, both to examine their efficacy, and to minimize undesirable effects attributable to one enantiomer or to the interaction of enantiomers in a racemic mixture. The United States Food and Drug Administration has recently issued new regulations governing the marketing of chiral drugs.

Separating optical isomers often requires considerable time, effort, and expense, even when state-of-the-art chiral separation techniques are used. There is a continuing and growing need for improved chiral separation techniques.

Early chiral separation methods used naturally occurring chiral species in otherwise standard separation protocols. For example, natural chiral polymeric adsorbents such as cellulose, other polysaccharides, and wool were used as early as the 1920's. Later strategies used other proteins and naturally occurring chiral materials. These early strategies gave some degree of success. However, the poor mechanical and chromatographic properties of naturally occurring materials often complicated the separations. Although naturally occurring chiral materials continue to be used for chiral separations, efforts have increasingly turned to synthesizing chiral materials having better mechanical and chromatographic properties. D. Armstrong, "Optical Isomer Separation by Liquid Chromatography," Anal. Chem., vol. 59, pp. 84A–91A (1987) gives a review of methods that have been used for chiral separations in liquid chromatography.

The two separation methods most often employed for chiral separations are high performance liquid chromatography and capillary electrophoresis, both of which have high efficiencies. High separation efficiencies are required for chiral separations because the difference in molar free energies of the interactions that discriminate between individual enantiomers is small, typically on the order of 100 calories per mole. The sum of the weighted time averages of these small interactions determines the overall enantioselectivity of a separation technique. High efficiencies are therefore important to improved chromatographic chiral separations. Separations on the order of 100,000 theoretical plates are readily achievable with capillary electrophoresis. Thus, small chiral selectivities can be magnified using capillary electrophoresis.

The so-called "three point rule" is a commonly used rule-of-thumb in many chiral recognition strategies. The "three point rule" recommends that there be a minimum of three simultaneous interactions between the chiral recognition medium and at least one of the enantiomers to be separated. In addition, at least one of the three interactions must be stereochemically dependent. The three interactions need not be attractive interactions, and may for example employ repulsion due to electrostatic or steric effects. For example, the "three point rule" was successfully used in 1971 in the design of a chiral stationary phase for the separation of the enantiomers of L-DOPA (L-dihydroxyphenylalanine). See R. J. Baczuk et al., "Liquid Chromatographic Resolution of Racemic β-3,4-Dihydroxyphenylalanine," J. Chromatog., vol. 60, pp. 351–361 (1971).

Until recently, the most common type of synthetic chiral stationary phase used in high performance liquid chromatography ("HPLC") was a Pirkle-type (Brush-type) phase. A Pirkle-type phase is based on the "three point rule," and usually employs $\pi$—$\pi$ interactions (electron donor-acceptor) and intermolecular hydrogen bonding in chiral recognition.

Another successful approach has used reversible complexes formed of metal ions and chiral complexing agents. This separation method is commonly called ligand-exchange-chromatography ("LEC"). LEC is usually explained by a model based on multicomponent complexes containing a central metal ion and two chelating chiral molecules. Enantiomers can be separated in LEC either by using chiral mobile phase additives, or by using a chiral stationary phase.

Host-guest enantioselective complexes, in either the mobile phase or the stationary phase, can also be used to separate individual enantiomers. Systems within this general category include those employing chiral crown ethers and cyclodextrins. Compared to crown ethers, cyclodextrins are relatively inexpensive, and are more readily derivatized. See E. Gassmann et al., "Electrokinetic Separation of Chiral Compounds," Science, vol. 230, pp. 813–814 (1985); and R. Kuhn et al., "Chiral Separation by Capillary Electrophoresis," Chromatographia, vol. 34, pp. 505–512 (1992). For example, D. Armstrong et al., "Enrichment of Enantiomers and Other Isomers with Aqueous Liquid Membranes Containing Cyclodextrin Carriers," Anal. Chem., vol. 59, pp. 2237–2241 (1987) disclose the use of an aqueous liquid membrane employing cyclodextrin carriers to perform an enantiomeric enrichment.

Micelles

Surfactants, molecules having both hydrophilic and hydrophobic groups, associate with one another in polar solvents such as water to form dynamic aggregates known as "micelles." A micelle typically takes roughly the shape of a sphere, a spheroid, an ellipsoid, or a rod, with the hydrophilic groups on the exterior and the hydrophobic groups on the interior. The hydrophobic interior provides, in effect, a hydrophobic liquid phase with solvation properties differing from those of the surrounding solvent. Micelles form when the concentration of the amphophilic molecules in solution is greater than a characteristic value known as the critical micelle concentration ("CMC").

Micelles have been used for a variety of purposes, including micellar catalysis; micelle-substrate interactions; and analytical applications such as spectroscopic analyses, electrochemical measurements, and separations. For example, K. Taguchi et al., "Immobilized Bilayer Stationary Phases in Gas Chromatography," J. Chem. Soc., Chem. Commun., pp. 364–365 (1986) disclose the use of an immobilized, stable, poly-ion complex containing vesicles for use in a gas chromatography column.

For a general discussion of micellar electrokinetic capillary chromatography, see S. Terabe et al., "Electrokinetic Chromatography with Micellar Solution and Open-Tubular Capillary," Anal. Chem., vol. 57, pp. 834–841 (1985); and S. Terabe et al., "Electrokinetic Separations with Micellar Solutions and Open-Tubular Capillaries," Anal. Chem., vol. 56, pp. 111–113 (1984).

Chiral Micelles

An important application of micelles is their use in chiral recognition and separation. Chiral surfactants have been used to form micelles having distinct chiral properties. The resulting chiral microenvironment has been shown to exhibit selective interactions with different enantiomers in solution. See, e.g., S. Terabe et al., "Chiral Separation by Electrokinetic Chromatography with Bile Salt Micelles," J. Chromatog., vol. 480, pp. 403–411 (1989); S. Terabe et al., "Separation of Enantiomers by Capillary Electrophoretic Techniques," J. Chromatog. A, vol. 666, pp. 295–319 (1994); T. Ward, "Chiral Media for Capillary Electrophoresis," Anal. Chem., vol. 66, pp. 632A–640A (1994); and M. Novotny et al., "Chiral Separation through Capillary Electromigration Methods," Anal. Chem., vol. 66, pp. 646A–655A (1994).

In addition to the equilibrium between micelles and ligands, there is also a dynamic equilibrium between surfactant molecules and micelles. "Conventional" micelles are dynamic aggregates of surfactant monomers; the monomers exist in equilibrium between aggregation in micelles, and being free in solution as smaller aggregates down to monomers. Because the difference in interactions between a chiral micelle and two enantiomers is often very small, these dynamic equilibria may interfere with the separation of enantiomers. See the schematic diagram of FIG. 1(a), in which an asterisk represents a chiral center, and S represents the solute.

Mixed chiral micelle systems have been reported to have enhanced resolving power as compared to the resolving power of micelles formed from the individual components. See K. Otsuka et al., "Enantiomeric Resolution by Micellar Electrokinetic Chromatography with Chiral Surfactants," J. Chromatog., vol. 515, pp. 221–226 (1990); and Y. Ishihama et al., "Enantiomeric Separation by Micellar Electrokinetic Chromatography Using Saponins," J. Liq. Chromatog., vol. 16, pp. 933–944 (1993).

Polymerized Micelles

Polymerized surfactant aggregates, or polymerized micelles, were first developed in the late 1970's and early 1980's. Compared to otherwise identical non-polymerized micelles ("conventional micelles"), polymerized micelles exhibit enhanced stability, enhanced rigidity, and better control over micelle size. The covalent bonds between surfactant monomers essentially eliminate the dynamic equilibrium between surfactant monomers and "conventional" micelles, simplifying and enhancing complexation between micelle and ligand.

An important advantage of polymerized micelles is that they have no critical micelle concentration ("CMC"). Because the individual surfactant monomers in a polymerized micelle must associate with one other, micelles form regardless of how low their concentration is. By contrast, with non-polymerized micelles the concentration of the surfactant must be higher than the CMC for a significant concentration of micelles to form. Furthermore, if the CMC of a charged surfactant is high, the high concentration of surfactant will generate considerable heat in micellar electrokinetic capillary chromatography (MECC), due to the high current resulting from the high charge density in solution. The heat generated can be deleterious to separations. By contrast, generation of heat with polymerized micelles can be greatly reduced because polymerized micelles have no CMC.

C. Palmer et al., "A Monomolecular Pseudostationary Phase for Micellar Electrokinetic Capillary Chromatography," J. High Res. Chromatog., vol. 15, pp. 756–762 (1992) discloses the use of an oligomerized sodium 10-undecylate micelle-like structure in micellar electrokinetic capillary chromatography. See also C. Larrabee et al., "Radiation-Induced Polymerization of Sodium 10-Undecenoate in Aqueous Micelle Solutions," J. Poly. Sci.: Poly. Lett. Ed., vol. 17, pp. 749–751 (1979).

Polymerized micelles are typically more rigid than conventional micelles, a property that may result in faster mass transfer. Polymerized micelles have a more compact structure than do conventional micelles. Thus solute molecules do not penetrate as deeply, which may result in faster mass transfer rates. See C. Paleos et al., "Comparative Studies between Monomeric and Polymeric Sodium 10-Undecenoate Micelles," J. Phys. Chem., vol. 87, pp. 251–254 (1983).

For other disclosures of polymerized micelles and their uses in separations, see also D. Tabor et al., "Some Factors in Solute Partitioning between Water and Micelles or Polymeric Micelle Analogues," Chromatog., vol. 20, pp. 73–80 (1989); S. Terabe et al., "Ion-Exchange Electrokinetic Chromatography with Polymer Ions for the Separation of Isomeric Ions Having Identical Electrophoretic Mobilities," Anal. Chem., vol. 62, pp. 650–652 (1990); J. Fendler et al., "Polymerized Surfactant Aggregates: Characterization and Utilization," Acc. Chem. Res., vol. 17, pp. 3–8 (1984); and C. Palmer et al., "A Monomolecular Pseudostationary Phase for Micellar Electrokinetic Capillary Chromatography," J. High Res. Chromatog., vol. 15, pp. 756–762 (1992).

Polymerized Chiral Micelles

Polymerized chiral micelles eliminate much of the complex dynamic behavior otherwise associated with micelles. Polymerized chiral micelles often have stronger chiral recognition properties than do otherwise-identical, "conventional" or non-polymerized chiral micelles.

In addition, recovery of chiral ligands from polymerized chiral micelles is often easier; the chiral ligands may typically be recovered by simple extraction with an appropriate organic solvent. By contrast, recovering the solute from a conventional, non-polymerized micellar medium by extraction with an organic solvent frequently causes the formation of troublesome emulsion systems. Polymerized chiral micelle systems are therefore beneficial in both preparative-scale and process-scale separations.

Enantiomeric separations employing polymerized chiral surfactants are disclosed in Wang, J.; Warner, I. M. Anal. Chem. 1994, 66, 3773–3776; Dobashi, A.; Hamada, M.; Dobashi, Y. Anal. Chem. 1995, 67, 3011–3017; and Wang, J.; Warner, I. M. J. Chromatog. 1995, 711, 297–304. See also commonly-assigned U.S. patent application Ser. No. 08/698, 351, now allowed with the issue fee paid; and Japanese patent applications 04149205 (May 1992) and 04149206 (May 1992).

Miscellaneous

Leydet, A. et al., J. Med. Chem. 1996, 39, 1626–1634 discloses a series of polyanions synthesized via γ-polymerization, in aqueous micellar solution, of ω-unsaturated anionic surfactants whose polar head was derived from certain amino acids or certain dipeptides; and the evaluation of the activity of these polyanions against human immunodeficiency virus and other RNA and DNA viruses. The polyanions evaluated included polymers of N-undec-10'-enoyl-L-prolyl-L-glutamic acid, N-undec-10'-enoyl-L-methionyl-L-glutamic acid, and N-undec-10'-enoyl-L-phenylalanyl-β-alanine.

Novel Chiral Separations Using Polymerized Chiral Micelles

It has been discovered that polymerized dipeptide or oligopeptide chiral surfactants greatly enhance the chiral separation of many racemic mixtures. The enhanced degree of chiral separation is surprising in comparison with the separations obtained with otherwise comparable polymerized single amino acid chiral surfactants.

BRIEF DESCRIPTION OF THE DRAWINGS

FIGS. 1(a) and 1(b) illustrate schematically the dynamic interactions associated with "conventional" chiral micelles and polymerized chiral micelles, respectively.

I. Separations of Basic, Acidic, and Neutral Racemic Mixtures

Figure 2:
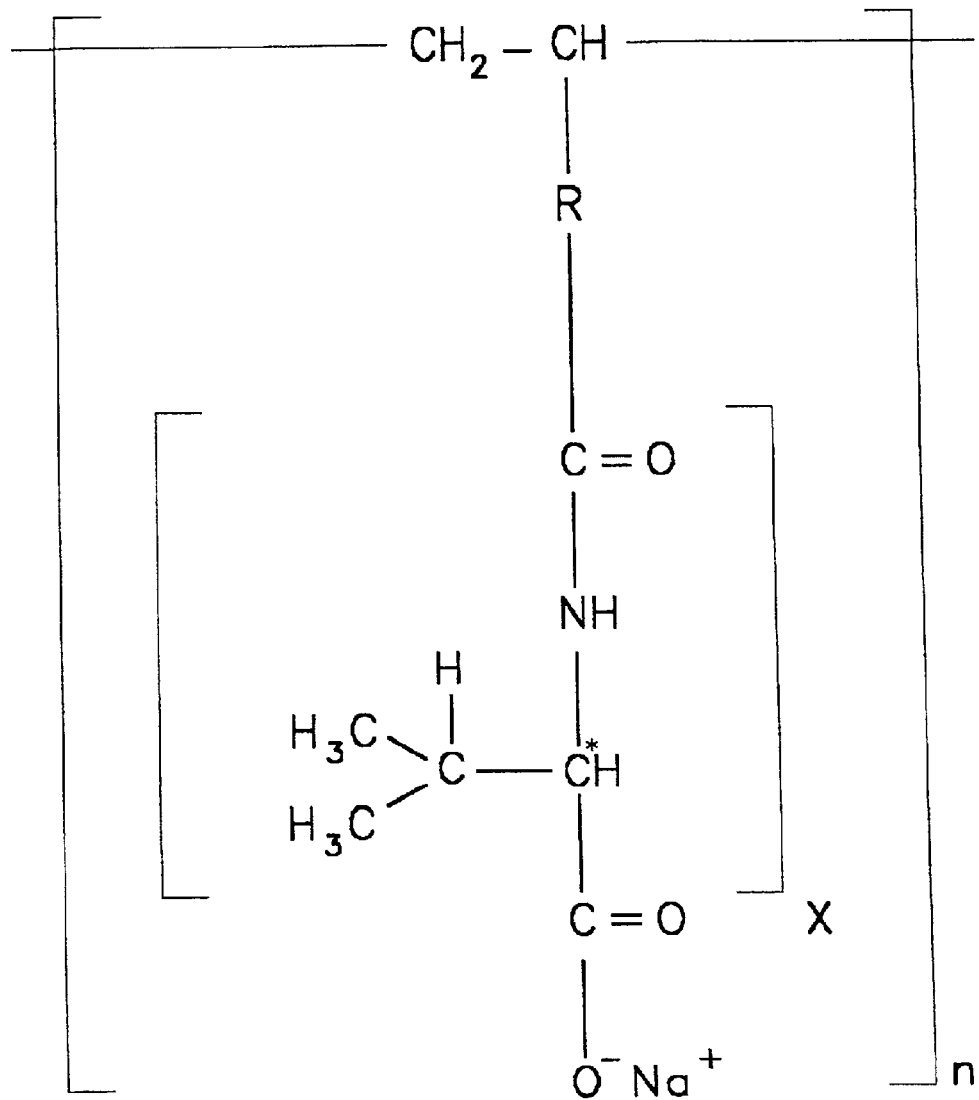
FIG. 2 depicts the structure of two polymeric chiral surfactants used in initial experiments comparing monopeptide surfactants to dipeptide surfactants.

FIG. 2 depicts the structure of two polymeric chiral surfactants used in initial experiments comparing monopeptide surfactants to dipeptide surfactants. The structural difference between poly(sodiumN-undecylenyl-L-valine-L-valine) (poly-L-SUV) and poly(sodiumN-undecylenyl-L-valine-valine) (poly-L-SUVV) is the number of valine amino acid groups attached to the hydrocarbon chain. Otherwise, the two compounds are similar. Both contain a polymerizable double bond at the end of the hydrocarbon tail. Poly-L-SUV contains one chiral center, namely that of the amino acid valine. Poly-L-SUVV is a dipeptide surfactant in which the a-carboxyl group of a first amino acid is attached to the α-amino group of a second amino acid by a peptide bond, resulting in two chiral centers of the same optical configuration. Both polymeric surfactants exist predominantly as monoanions at pH≧6 due to a single ionizable carboxyl group.

In prototype tests, we compared the chiral separation behaviors of two cationic racemic mixtures (±propanolol (PROP) and ±alprenolol (ALP)), one anionic racemic mixture (±1,1'-binaphthyl-2,2'-diyl hydrogen phosphate (BNP)), and one nonionic racemic mixture ((±trifluoro-1-(9-anthryl)ethanol) (TFAE)).

Materials

The analytes (±)-1,1'-binaphthyl-2,2'-diyl hydrogen phosphate (BNP, 99%), propranolol (PROP, 99%), and trifluoro-1-(9-anthryl)ethanol (TFAE, 98+%) were purchased from Aldrich Chemical Company (Milwaukee, Wis.). The racemic mixture of (±)-alprenolol (ALP, 99%) was obtained from Sigma (St. Louis, Mo.). All analytes were used as received. Buffers ($Na_2HPO_4$, $Na_2B_4O_7$) used as background electrolytes (BGEs) were of analytical reagent grade, and were also obtained from Sigma. The migration order for each enantiomer was established by spiking the racemic mixture with excess (+) or (−) enantiomer, also obtained from either Sigma or Aldrich. The monosodium salt of naphthalene-monosulfonate (NMS, 99.5% purity) was purchased from American Tokyo Kasei (Portland, Oreg.). This compound was used as a light-absorbing electrolyte to detect monomeric surfactants.

Synthesis of Poly(sodium N-undecyl-L-valine) and Poly(sodium N-undecyl-L-valine-L-valine)

The mono-amino acid surfactant N-undecylenyl-L-valine (L-UV), was synthesized according to the procedure of Wang, J.; Warner, I. M. *Anal. Chem.* 1994, 66, 3773–3776, with some modifications. A similar procedure was used for the synthesis of the dipeptide surfactant, N-undecylenyl-L-valine-valine (L-UVV). The modified synthetic strategies for L-UV and L-UVV were essentially similar to the published synthesis cited above, except for a modification in the last step, preparing the sodium salts of L-UV and L-UVV. These sodium salts were prepared by converting the corresponding acids using equimolar amounts of $NaHCO_3$ (instead of NaOH) in a tetrahydrofuran:water mixture (instead of ethanol:water). The solvent mixture was stirred overnight, and THF was removed by roto-evaporation. The remaining aqueous solutions of both surfactants were freeze-dried to give L-SUV and L-SUVV.

The acid forms of both L-UV and L-UVV were then converted to the corresponding sodium salt formed by adding an equimolar solution of sodium bicarbonate in the presence of THF, followed by solvent evaporation and freeze-drying to obtain the desired L-SUV and L-SUVV surfactants. Polymerization of both surfactants was achieved by $^{60}Co$ γ-irradiation (70 krad/hr), for 36–48 hours (total dose: 3–4 Mrad) of 100 mM solutions of the surfactants. After irradiation, both poly-L-SUV and poly-L-SUVV solutions were dialyzed against bulk $H_2O$ using a regenerated cellulose membrane with a 2000 molecular weight cutoff. Finally, the dialyzed products were lyophilized to obtain dry poly-L-SUV and poly-L-SUVV.

Proton NMR spectroscopy was used to follow the polymerization process. For both poly-L-SUV and poly-L-SUVV surfactants, NMR indicated the disappearance of the double bond proton signals at 5.8 and 5.0 ppm. Polymerization also broadened the remaining peaks. The polymers were 99% pure, as calculated from elemental analysis.

Electrokinetic Chromatography Instrumentation

A Beckman (Fullerton, Calif.) P/ACE Model 5510 capillary electrophoresis (CE) instrument was used in electrokinetic chromatography (EKC) to separate (±)-BNP. This CE instrument was equipped with: (1) a 0–30 kV high-voltage built-in power supply; (2) 200, 214, 254 and 280 nm selectable wavelength filters for V detection; and (3) System Gold software for system control and data handling.

The enantiomeric separations of (±) PROP, (±)-ALP and (±)-TFAE were performed on a Hewlett-Packard (HP) (Palo Alto, Calif.), 3D-CE instrument. Data processing for the HP instrument was performed by an HP Vectra personal computer (5/90) with HPCE Chemstation software. Separations in both the Beckman and the HP instruments used uncoated fused-silica capillaries (Polymicro Technologies, Phoenix, Ariz.) of 50 μm i.d. with total lengths of 47 cm and 64 cm, (40 cm and 60 cm to detector window ($L_d$)), respectively. The temperature of the capillary in the Beckman instrument was maintained with a fluoroorganic fluid, and the HP instrument was equipped with a Peltier element for forced air cooling and temperature control of the capillary. The study of the reverse migration order of (±)-BNP was performed with a poly(vinyl alcohol) (PVA)-coated capillary 50 μm×64.5 cm (56 cm $L_d$) purchased from HP.

Capillary Electrophoresis Procedures

All new capillaries were washed in a standard cycle of 1N NaOH for one hour before use. It was also a daily routine procedure to flush the capillary with 1N NaOH (15 minutes), triply deionized water (2 minutes), and the running EKC buffer (10 minutes). For separations performed at pH≦7.0, the capillary was flushed with EKC buffer (only) for 3 minutes between injections. For separations performed at a pH between 8–10, the capillary was flushed for 3 minutes each with 0.1N NaOH and the EKC buffer. These procedures improved peak shapes, and enhanced the reproducibility of migration times in a range of 1.0–1.7% RSD, n=5.

Preparation of EKC Buffers and Standard Solutions

For all EKC experiments, the BGE was either dibasic sodium phosphate or borate buffer. Before adjusting the pH of the buffers, the appropriate percentage (w/v) of poly-L-SUV or poly-L-SUVV was added to the BGE. The pH was adjusted by adding HCl or NaOH to the BGE with the polymeric surfactant. After adjusting the pH, the final EKC running buffers were filtered through a 0.45 μm nylon syringe filter (Nalgene, Rochester, N.Y.) by creating a vacuum inside the syringe. After filtering, the solution was ultrasonicated for about 10 minutes to degas the buffers.

All stock solutions were prepared in 50% (v/v) methanol/water at concentrations of about 1–2 mg/mL each. Stock solutions were diluted as needed with a 50% (v/v) methanol/water mixture.

Calculations

The migration factors (k'), resolution factor ($R_s$) and N were calculated using the following equations:

$$k' = (t_r/t_o) - 1$$

$$R_s = 2(t_{r2} - t_{r1})/(w_1 + w_2)$$

$$N = 5.54(t_r/w_{1/2})^2$$

where $t_o$ and $t_r$ are the respective migration times of the unretained species and the enantiomer; w is the peak width at the baseline of each enantiomer designated as "1" and "2," respectively, and $w_{1/2}$ denotes the peak width at half height.

Physicochemical Properties of Monomeric Chiral Surfactants

Table 1 compares the structural features and physicochemical properties of L-SUV and L-SUVV. The critical micelle concentration ("CMC") for both chiral surfactants was measured by following a linear decrease in surface tension as surfactant concentration increased, up to a point. After this point, no appreciable change in surface tension was observed. The point of intersection of the two lines (the linear decrease and the flat line thereafter) was taken as the CMC of the surfactants. The greater hydrophobicity of L-SUVV compared to L-SUV gave the former a lower CMC. In addition, an increase in the molecular weight decreased the mobility of L-SUVV toward the injector end.

Thus, L-SUVV eluted faster than L-SUV, as it was carried more rapidly by bulk electroosmotic flow (EOF) towards the detection window. As discussed in greater detail below, we found that optical resolutions of enantiomers with L-SUVV were substantially enhanced as compared to L-SUV.

TABLE 1

Comparison of the Physicochemical Properties of Undecylenyl-L-valine (L-U-Val) and Undecylenyl-L-valine-valine (L-U-Val-Val) Monomeric Surfactants

| Characteristic | L-U-Val | L-U-Val-Val |
|---|---|---|
| molecular weight | 305 | 404 |
| number of stereogenic centers | 1 | 2 |
| hydrophobic tail | 1 | 1 |
| number of amido groups | 1 | 2 |
| number of carboxylic groups | 1 | 1 |
| critical micelle concentration[a] (CMC) [mM] | 13 | 10 |
| optical rotation $[\alpha]_D^{25}$ | −5.29° | −26.14° |
| effective electrophoretic mobility[b] ($\mu_{ep}$) [cm$^{-2}$ V$^{-1}$ s$^{-1}$] | −1.5 × 10$^{-4}$ | −1.2 × 10$^{-4}$ |

[a]Determined in pure water using surface tension measurement.
[b]Determined using capillary zone electrophoresis/indirect photometric detection at 280 nm, using NMS as light-absorbing electrolyte in 100 mM boric acid and 5 mM Na$_2$B$_4$O$_7$, pH 8.0. Methanol was used as the EOF marker.

Selection of Buffer pH for EKC Separations

Buffer pH was an important factor in EKC separations of basic, acidic, and neutral optical isomers. Changes in pH can affect the charge on both the analyte and the chiral pseudo-phase. In addition, polymer conformation and EOF may also vary with changes in pH. To try to optimize the pH for the separation of basic, acidic, and neutral enantiomers, we conducted studies in which 0.5% (w/v) of poly-L-SUV or poly-L-SUVV was added to phosphate or borate buffer over a pH range of 5.5 to 11.0 (data not shown). Acidic pH values (below 5.5) were not used, because the surfactants tended to precipitate. Based on our pH optimization study, enantioseparation of the cationic enantiomers (PROP and ALP) was found to be optimal at about pH 9.2. The anionic (BNP) and the neutral (TFAE) enantiomers were best resolved at pH values of 7.0 and 10.2, respectively. At optimum pH for each enantiomer, we conducted further experiments to find optimal concentrations and types of polymeric chiral pseudo-phases, and optimal BGE concentration. The details of these optimization procedures are described below.

Separation of Basic Enantiomers

PROP and ALP are examples of basic drugs that are commonly called beta-adrenergic blockers (β-blockers). These cationic drugs have been used for the treatment of hypertension. Typically, the (S)-(−) enantiomer is more potent than the (R)-(+) form; the latter may be toxic. PROP and ALP possess similar structural features: an alkanolamine side-chain terminating in a secondary amino group and an aromatic group (see FIG. 3). The p$K_a$ value of the ionizable nitrogen is around 9.2–9.6. The best pH for enantioseparation was near the p$K_a$ of these compounds. As indicated above, a pH around 9.2 was found to be optimal for these separations.

Table 2 provides electrokinetic data for the separation of PROP enantiomers under analogous pH and BGE concentrations for various concentrations of poly-L-SUV and poly-L-SUVV. Where chiral resolution was achieved, the k' and N values given in Table 2 are those for the first enantiomer of PROP. As expected for an electrokinetic separation, increasing the concentration of the polymeric chiral anionic pseudo-phase (poly-L-SUV or poly-L-SUVV) increased the k' for PROP. This effect is directly related to an increase in the hydrophobic and electrostatic interactions of this positively charged racemate with the polymeric anionic surfactant. Although poly-L-SUVV is relatively more hydrophobic than poly-L-SUV, the dipeptide poly-L-SUVV almost always resulted in separations of PROP enantiomers with shorter k' values and much improved resolutions under equivalent monomer concentrations. Similar trends for k' were also seen for ALP enantiomers (data not shown).

TABLE 2

Comparison of Migration Factors, Resolution, and Efficiency for Propranolol Enantiomers, Obtained Using Various Concentrations of Poly-L-SUV and Poly-L-SUVV Surfactants[a]

| Concentration [% (w/v)] | Equivalent Monomer Concentration [mM] | k' | $R_s$ | N |
|---|---|---|---|---|
| 0.075 poly-L-Suv | 2.5 | 0.63 | 0.0 | 107 500 |
| 0.10 poly-L-SUVV | | 0.64 | 1.1 | 104 060 |
| 0.19 poly-L-SUV | 6.2 | 1.69 | 0.0 | 113 500 |
| 0.25 poly-L-SUVV | | 1.36 | 1.5 | 186 500 |
| 0.38 poly-L-SUV | 12.4 | 3.20 | 0.0 | 114 200 |
| 0.50 poly-L-SUVV | | 2.03 | 2.3 | 290 000 |
| 0.57 poly-L-SUV | 18.6 | 4.80 | 0.0 | 116 600 |
| 0.75 poly-L-SUVV | | 2.53 | 1.7 | 248 600 |
| 0.76 poly-L-SUV | 24.8 | 7.02 | 0.1 | 127 400 |
| 1.00 poly-L-SUVV | | 2.99 | 1.4 | 231 700 |

[a]Using 50 mM $Na_2B_4O_7$ buffered at pH 9.2. Pressure injection for 2 s (0.1 mg/mL) for propranolol. Separation voltage, +20 kV; current, 50–87 µA. Detection was at 214 nm.

Figure 3:
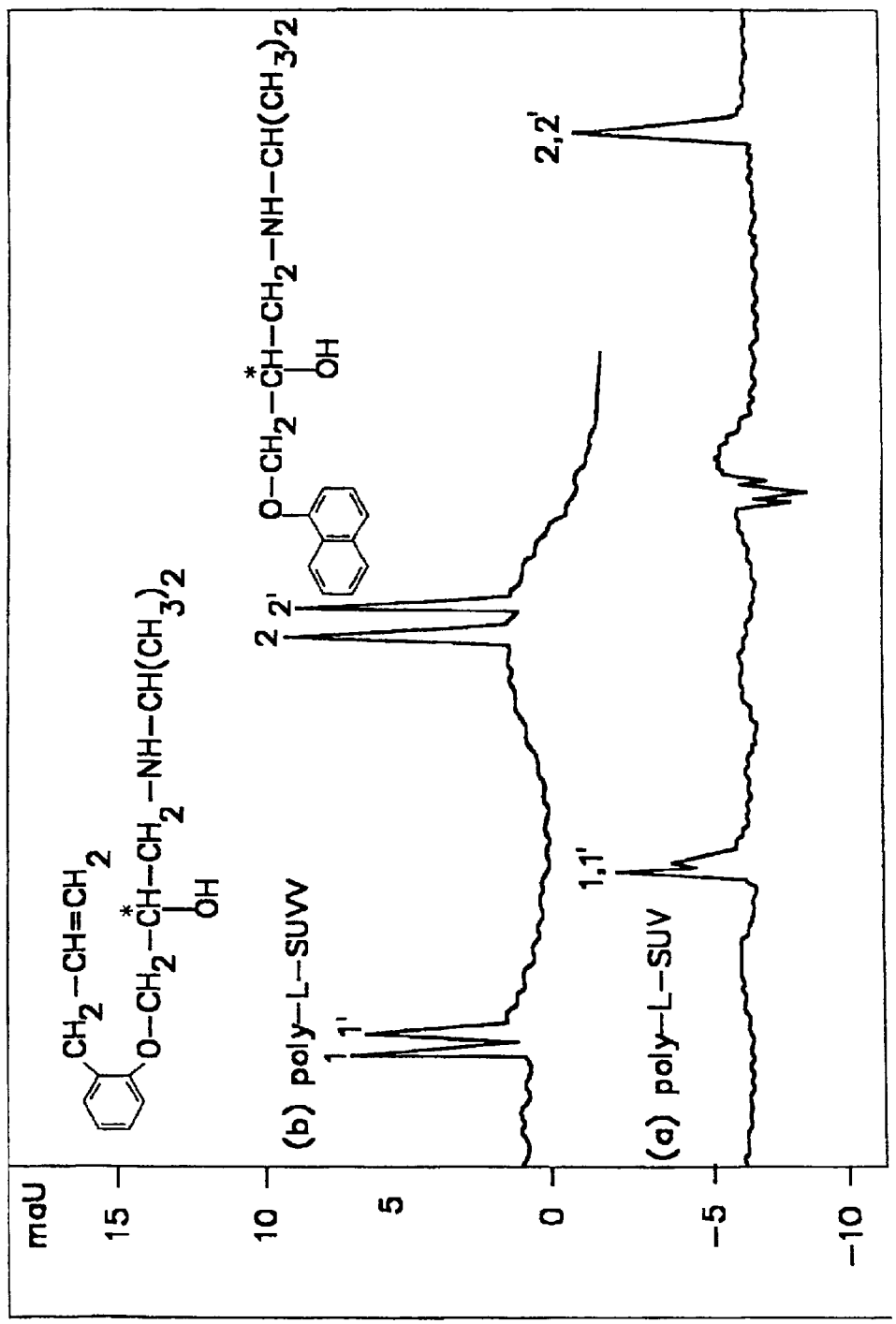
FIG. 3 depicts electrokinetic chromatograms for the simultaneous separations of the ALP and PROP enantiomers using optimized concentrations of poly-L-SUV and poly-L-SUVV surfactants.

Baseline resolutions ($R_s$>1.5) with the highest N values were obtained for both PROP enantiomers at 0.5% (w/v) of poly-L-SUVV. By contrast, no $R_s$ for PROP was found at any concentration of the poly-L-SUV surfactant. Higher concentrations (>1% (w/v)) of either polymer did not improve the $R_s$, but led to markedly longer k' values. FIG. 3 compares the electrokinetic chromatograms for the simultaneous separations of the ALP and PROP enantiomers using optimized concentrations of poly-L-SUV and poly-L-SUVV surfactants. Using either of these surfactants, (±)-ALP and (±)-PROP eluted in order of increasing hydrophobicity. However, the (S)-(–) enantiomer of each racemate eluted faster than the corresponding (R)-(+) forms. The migration times and order were a direct consequence of the analyte/surfactant binding. Furthermore, an increase in the migration time for either (±)-ALP or (±)-PROP enantiomers with poly-L-SUV did not lead to enhanced chiral separations. By contrast, the separations of both pairs of enantiomers with L-SUVV were fairly sharp.

The improved chiral resolution and decreased migration time for cationic racemates using poly-L-SUVV suggested that the retention mechanism for, and the chiral recognition of such analytes are controlled by steric factors rather than by the hydrophobicity of the chiral pseudo-phase. Probably, a relatively milder electrostatic attraction between the anionic poly-L-SUVV surfactants with the cationic racemates results in a lower k' value, and better chiral discrimination than those obtained with poly-L-SUV surfactants. In addition, it is probable that the greater number of chiral centers and hydrogen bonding sites on the ionic head group in poly-L-SUVV also contributed to its superior chiral discrimination as compared to poly-L-SUV.

The k', $R_s$, and N values of both ALP and PROP enantiomers were further optimized by varying the concentration of borate buffer serving as the BGE. As the borate concentration increased from 5 to 50 mM, the k' and $R_s$ values for the two cationic racemates increased at the expense of some decrease in N. Further increases in borate concentration from 75 to 100 nM decreased both $R_s$ and N for ALP enantiomers, but slightly improved $R_s$ for PROP enantiomers was noted. The reduction in $R_s$ and N can be explained by the observed increase in peak widths, which in turn is caused by a reduction in EOF and an increase in the viscosity of the electrolyte. Joule heating at high ionic strength is another factor that contributes to a decrease in $R_s$ and N values, as was experimentally confirmed by plotting current as a function of applied voltage at 100 mM borate. The plot showed a significant deviation from linearity around 12 kV. A borate buffer concentration of about 50 mM was found to be optimal for the $R_s$ of ALP and PROP enantiomers.

To improve the signal-to-noise ratio (S/N) of separations of ALP and PROP enantiomers, we conducted experiments to determine injection times that could be conveniently employed without sacrificing $R_s$. There is a tradeoff between $R_s$ and S/N. Loading less analyte onto the capillary substantially improves the $R_s$ between the enantiomers. S/N deteriorates with longer injection times. The optimal injection size to resolve a particular racemate depends on the molar absorptivity of the racemate. A racemate with higher molar absorptivity can be injected at lower concentrations and improve the $R_s$. For instance, the separation of ALP enantiomers injected at concentrations of 0.2 mg/mL began to degrade rapidly without any improvement in S/N around an injection time of 6 seconds. In contrast, the separation of PROP enantiomers injected at concentrations of 0.1 mg/mL using the same injection size was still quite reasonable. However, as the injection time of PROP enantiomers was increased above 12 seconds, peak fronting became very pronounced and the $R_s$ degraded significantly.

TABLE 3

Comparison of Migration Factors, Resolution, and Efficiency for Alprenolol and Propranolol Enantiomers, Obtained Using Various Concentrations of Borate Buffer[a]

| Concentration [mM] | k' | $R_s$ | N |
|---|---|---|---|
| Alprenolol | | | |
| 5.0 | 1.06 | 0.2 | 319 600 |
| 12.5 | 1.12 | 0.5 | 329 900 |
| 25.0 | 1.19 | 0.7 | 155 540 |
| 50.0 | 1.39 | 1.5 | 136 000 |
| 75.0 | 1.44 | 1.2 | 75 300 |
| 100.0 | 1.57 | 0.9 | 65 800 |
| Propranolol | | | |
| 5.0 | 1.14 | 0.3 | 550 600 |
| 12.5 | 1.30 | 0.5 | 650 200 |
| 25.0 | 1.53 | 0.9 | 312 700 |
| 50.0 | 2.03 | 2.3 | 290 000 |
| 75.0 | 2.44 | 2.5 | 194 800 |
| 100.0 | 3.01 | 2.6 | 104 600 |

[a]Using the optimized 0.5% (w/v) poly-L-SUVV containing variable concentration of $Na_2B_4O_7$ buffered at pH 9.2. Pressure injection for 2 s, 0.2 mg/mL for alprenolol and 0.1 mg/mL for propranolol. Separation voltage, +20 kV; current, 10–102 µA. Detection was at 214 nm.

Separation of Acidic Enantiomers

Many chiral molecules lack an asymmetric carbon center. For example, atropisomeric binaphthyl compounds such as BNP belong to a class of molecules that are chiral because they possess adjacent π systems that cannot adopt a coplanar configuration due to steric hindrance and rotational restrictions around a central bond. (See FIG. 4(b)). Racemic BNP has been used as a chiral shift reagent for determining the enantiomeric purity of other compounds. BNP has also been used as a ligand in asymmetric catalysts, and as a building block in synthesizing macrocyclic compounds. The enantiomers of (±)-BNP predominantly exist in anionic form at the optimal pH of 7.0 used in the experiments reported here.

Chiral separations of negatively charged (±)-BNP were compared using poly-L-SUV and poly-L-SUVV at the optimized pH of 7.0. Table 4 shows the influence of the type and concentration of polymeric chiral pseudophase on the k', $R_s$, and N of BNP enantiomers. Again, k' and $R_s$ both increased with increasing concentrations of poly-L-SUV or poly-L-SUVV. At each concentration, substantially better $R_s$ values were obtained with the dipeptide than with the single amino acid surfactant. For example, (±)-BNP showed a baseline $R_s$ of 1.5 even at 0.25% (w/v) of poly-L-SUVV, while no $R_s$ of the same enantiomers was possible at equivalent concentrations of poly-L-SUV. Table 4 also shows that for each polymeric surfactant, there was an optimum concentration at which chiral $R_s$ reached a maximum value. A maximum $R_s$ of 3.2 was obtained for (±)-BNP at 1.50% (w/v) of poly-L-SUVV. A maximum $R_s$ of only 1.2 was obtained for poly-L-SUV, at a concentration of 1.13% (w/v).

TABLE 4

Comparison of Migration Factors, Resolution, and Efficiency for Binaphthol Phosphate (BNP) Enantiomers Using Various Concentrations of Poly-L-SUV and Poly-L-SUVV Surfactants[a]

| Concentration [% (w/v)] | Equivalent Monomer Concentration [mM] | k' | $R_s$ | N |
|---|---|---|---|---|
| 0.19 poly-L-Suv | 6.2 | 1.25 | 0.1 | 101 000 |
| 0.25 poly-L-SUVV | | 1.46 | 1.5 | 114 000 |
| 0.38 poly-L-SUV | 12.4 | 1.65 | 0.5 | 135 000 |
| 0.50 poly-L-SUVV | | 1.87 | 2.2 | 140 000 |
| 0.76 poly-L-SUV | 24.8 | 2.46 | 0.7 | 167 000 |
| 1.00 poly-L-SUVV | | 2.67 | 3.0 | 172 000 |
| 1.13 poly-L-SUV | 37.2 | 3.42 | 1.2 | 175 000 |
| 1.50 poly-L-SUVV | | 3.81 | 3.2 | 87 400 |
| 2.26 poly-L-SUV | 74.4 | 10.43 | 0.6 | 69 000 |
| 3.00 poly-L-SUVV | | 11.30 | 3.1 | 60 000 |

[a]Using 50 mM phosphate (NaH$_2$PO$_4$/Na$_2$HPO$_4$) buffered at pH 7.0. Pressure injection for 4 s (0.1 mg/mL) for BNP racemate. Separation voltage, +20 kV; current, 44–78 μA. Detection was at 214 nm.

The k' values reported in Table 4 for (±)-BNP were higher for poly-L-SUVV than with poly-L-SUV at equivalent monomer concentrations. This observation is consistent with the theory that an increase in the hydrophobicity of the pseudo-stationary phase should increase the k' values. Note that this tendency is opposite to that seen in Table 2 for cationic enantiomers.

Figure 4A:
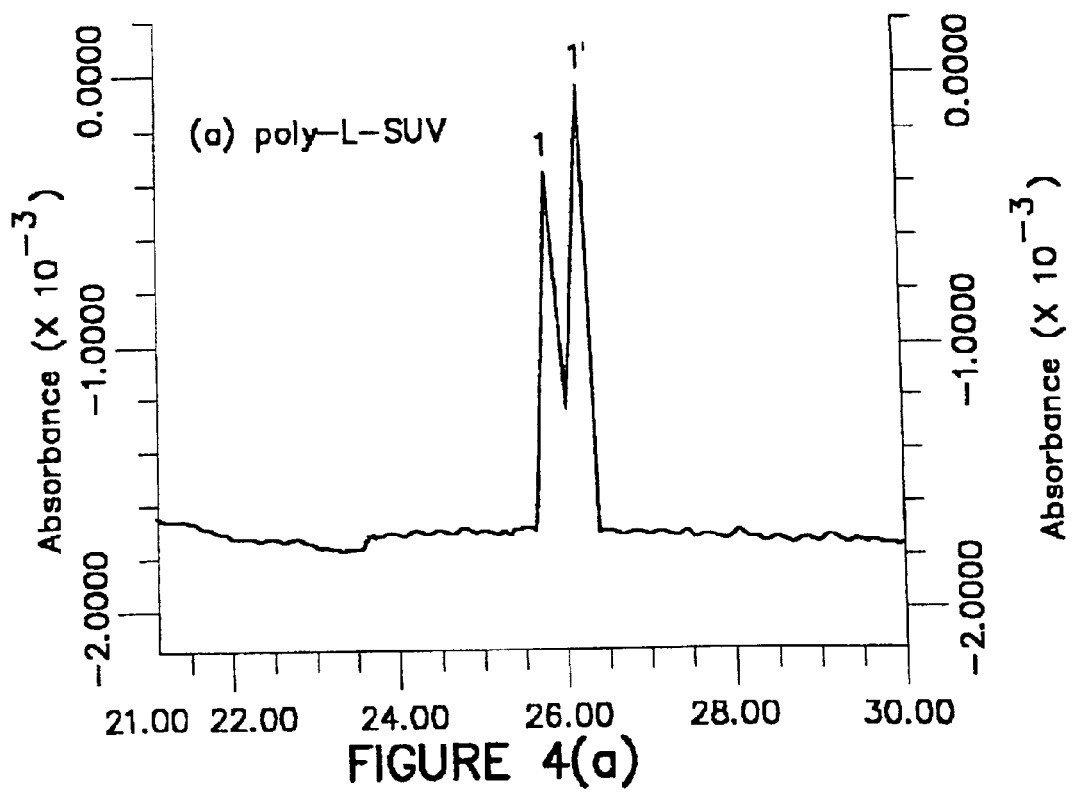
FIGS. 4(a) and 4(b) depict electrokinetic chromatograms for (±)-BNP at the optimized $R_s$ of 1.2 and 3.0 for poly-L-SUV and for poly-L-SUVV, respectively.
Figure 4B:
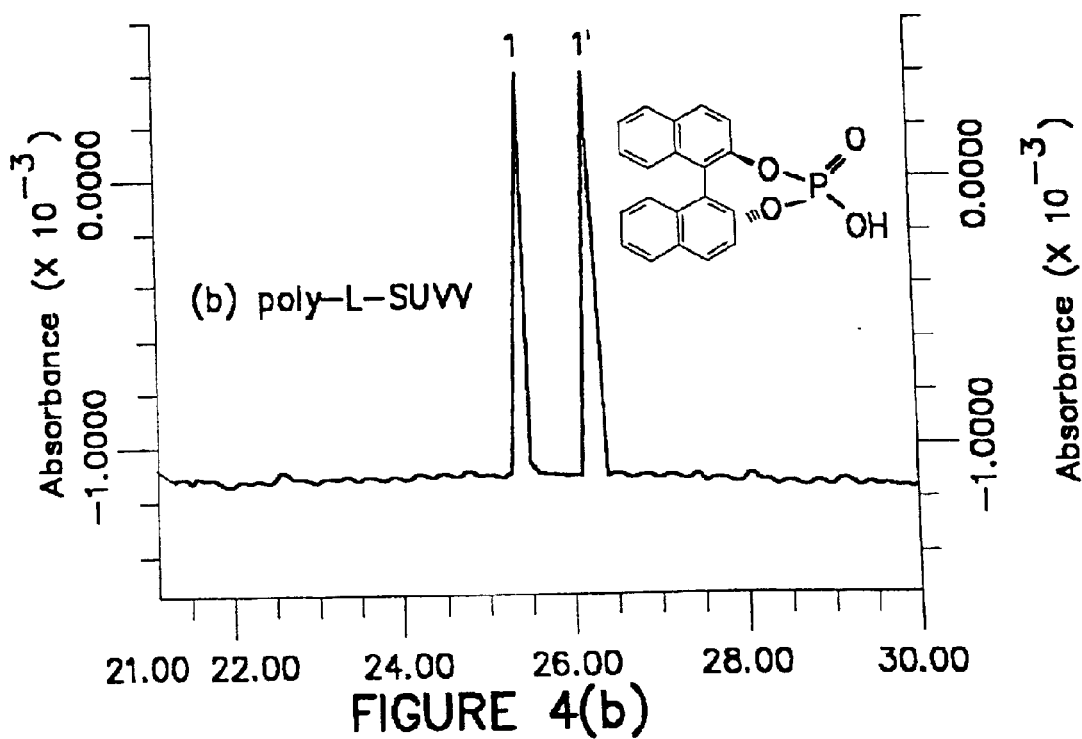

FIGS. 4(a) and 4(b) illustrate typical electrokinetic chromatograms for (±)-BNP at the optimized $R_s$ of 1.2 and 3.0 for poly-L-SUV and for poly-L-SUVV, respectively. Note again the much better separation and higher selectivity obtained with poly-L-SUVV as compared to poly-L-SUV. The successful enantioseparation of negatively charged (±)-BNP with an anionic polymerized surfactant confirms that, although electrostatic attractive interactions can contribute to the binding of charged analytes with oppositely charged polymerized surfactants, these interactions are not always the major force in chiral recognition. The highly hydrophobic naphthyl moiety and the hydrogen bonding capability of the phosphate group in (±)-BNP are probably major factors in chiral discrimination.

We also investigated the effect of phosphate buffer as a BGE for the poly-L-SUVV surfactant. Table 5 shows that the $R_s$ for (±)-BNP enantiomers could be increased as high as 4.5 with increased phosphate buffer concentrations. However, the increased R was obtained at the expense of longer analysis times and reduced N. Buffer concentrations of 25–50 mM provided a good overall working range, as the $R_s$ at those concentrations is more than sufficient, and a shorter analysis time is required. Much faster separations, with $R_s$=1.8 and an analysis time under 10 minutes (k'= 1.10), was still possible for (±)-BNP when the concentration of the phosphate buffer was as low as 2.5 mM.

TABLE 5

Comparison of Migration Factors, Resolution, and Efficiency for Binaphthol Phosphate (BNP) Enantiomers, Obtained Using Various Concentrations of Phosphate Buffer[a]

| Concentration [mM] | k' | $R_s$ | N |
|---|---|---|---|
| 2.5 | 1.10 | 1.8 | 200 000 |
| 5.0 | 1.17 | 1.9 | 201 000 |
| 10.0 | 1.33 | 2.2 | 225 000 |
| 25.0 | 2.29 | 3.0 | 190 000 |
| 50.0 | 2.67 | 3.0 | 172 000 |
| 100.0 | 5.21 | 3.7 | 90 000 |
| 150.0 | 9.75 | 4.5 | 47 000 |

[a]Using the optimized 1% (w/v) poly-L-SUVV containing equimolar concentration of phosphate (NaH$_2$PO$_4$/Na$_2$HPO$_4$), buffered at pH 7.0. Pressure injection for 4 s (0.1 mg/mL) for BNP. Separation voltage, +20 kV; current, 14–200 μA. Detection was at 214 nm.

It is important to control conditions that can cause reversal of the elution order of enantiomers, particularly when one is detecting trace-level enantiomeric impurities. In CE, altering pH and using chiral selectors with opposite configurations (D and L) can reverse the migration order. Another cause of reversed migration order can be the use of coated capillaries with suppressed or zero EOF. In particular, we studied the separation of (±)-BNP in a zero EOF environment, using a polyvinyl alcohol-coated capillary. Although the $L_d$ of the coated capillary was about 15 cm shorter, the analysis time was 10 minutes faster than on an uncoated capillary. The reduction in analysis time was probably due to the use of a negative polarity on the power supply. With such a configuration, both poly-L-SUV and the analyte (±)-BNP have a natural mobility toward the anodic end (i.e., the detector end used in negative polarity CE). We also found that the use of the shorter wavelength of 214 nm improved the S/N of (±)-BNP by factors of 10 and 8 as compared to that seen at 254 nm and 280 nm, respectively, due to the higher molar absorptivity of (±)-BNP at 214 nm. However, baseline stability was not as good at this wavelength as it was at 254 nm or 280 nm, due to some background absorbance from poly-L-SUVV.

Separation of Neutral Enantiomers

Figure 5A:
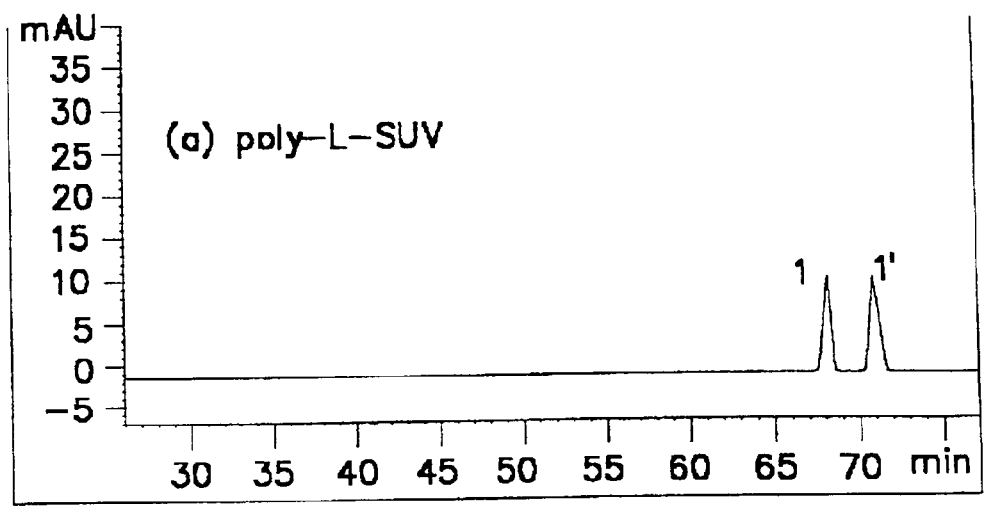
FIGS. 5(a) and 5(b) depict the separation of (±)-TFAE at optimized $R_s$ values of 2.5 and 2.1 using poly-L-SUV and poly-L-SUVV surfactants, respectively.
Figure 5B:
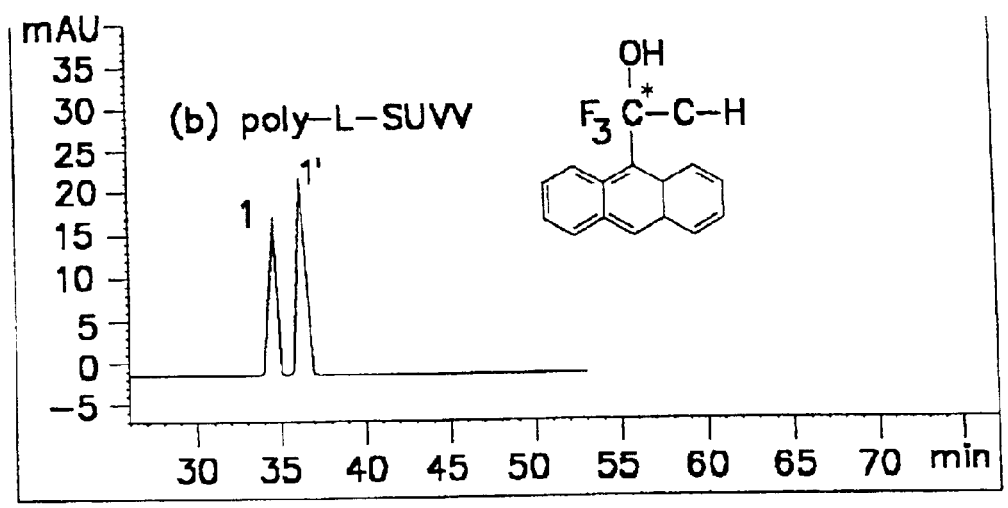

We compared the effects of poly-L-SUV and poly-L-SUVV surfactants on the chiral separation of a racemic mixture of (±)-TFAE, a neutral racemate (see FIG. 5(b)). TFAE enantiomers have been used as chiral NMR solvating agents for discriminating the enantiomeric purity of optically active compounds. Table 6 compares the effect of surfactant concentrations (at optimized pH and BGE concentrations) for both polymerized chiral surfactants on k', $R_s$, and N values for (±)-TFAE. In general, both k' and N for (±)-TFAE increased gradually with an increase in concentration of both polymers. At equivalent monomer concentrations the values of k' and N for (±)-TFAE were higher for poly-L-SUVV than for poly-L-SUV. However, the enantiomeric $R_s$ increased only slightly with increasing concentrations of poly-L-SUV from 0.075–0.38% (w/v), and remained unchanged for poly-L-SUVV in the concentration range of 0.10–0.50% (w/v). Further increases in concentration of both polymers decreased the $R_s$ of (±)-TFAE. FIGS. 5(a) and 5(b) compare the separation of (±)-TFAE at optimized $R_s$ values of 2.5 and 2.1 using poly-L-SUV and poly-L-SUVV surfactants, respectively. It is interesting to note that the higher $R_s$ of (±)-TFAE using poly-L-SUV, as compared to poly-L-SUVV, occurred only at the expense of longer analysis time and lower electrokinetic efficiency.

TABLE 6

Comparison of Migration Factors, Resolutions, and Efficiencies for Trifluoro-1-(9-anthryl)ethanol (TFAE) Enantiomers, Obtained Using Various Concentrations of Poly-L-SUV and Poly-L-SUVV Surfactants[a]

| Concentration [% (w/v)] | Equivalent Monomer Concentration [mM] | k' | $R_s$ | N |
|---|---|---|---|---|
| 0.075 poly-L-SUV | 2.5 | 3.56 | 1.9 | 38 450 |
| 0.10 poly-L-SUVV | | 3.66 | 2.1 | 59 800 |
| 0.19 poly-L-SUV | 6.2 | 4.62 | 2.1 | 46 200 |
| 0.25 poly-L-SUVV | | 4.83 | 2.1 | 59 380 |
| 0.38 poly-L-SUV | 12.4 | 7.23 | 2.5 | 49 200 |
| 0.50 poly-L-SUVV | | 8.02 | 2.1 | 61 530 |
| 0.76 poly-L-SUV | 24.8 | 8.10 | 2.0 | 40 600 |
| 1.00 poly-L-SUVV | | 8.79 | 1.7 | 55 700 |

[a]Using 50 mM sodium borate ($Na_2B_4O_7$) buffered at pH 10.2. Pressure injection for 4 s (0.1 mg/mL) for TFAE racemate. Separation voltage, +20 kV; current, 78–86 µA. Detection was at 254 nm.

II. The Effect of Amino Acid Order

We also investigated the effect of the order of the amino acids in dipeptide surfactants on chiral separation. The two main dipeptide surfactants used in this study were poly sodium N-undecylenyl-L-valine-L-leucine (poly (L-SUVL)), and poly sodium N-undecylenyl-L-leucine-L-valine, (poly (L-SULV)). Enantiomeric separations of two atropisomers, (±) 1,1'-bi-2-naphthol (BOH) and (±) 1,1'-bi-2-naphthyl-2,2'-diyl hydrogen phosphate (BNP) were compared with these polymerized surfactants. We also examined similarities and differences with the related polymerized surfactants sodium N-undecylenyl-L-leucine-L-leucine (L-SULL), sodium N-undecylenyl-L-valine-L-valine (L-SUVV), sodium N-undecylenyl-L-valine (L-SUV), and sodium N-undecylenyl-L-leucine (L-SUL).

Synthesis of Polymerized Surfactants

All surfactants in this study were synthesized according to the procedure of Wang, J.; Warner, I. M. *Anal. Chem.* 1994, 66, 3773–3776. Surfactant monomers were prepared by mixing the N-hydroxysuccinimide ester of undecylenic acid with the appropriate amino acid or dipeptide to form the corresponding N-undecylenyl chiral surfactant. The critical micelle concentrations of the surfactants were determined by surface tension measurements as previously described. Polymerization was induced with [60]Co γ-irradiation as previously described. Polymers were purified by dialysis using a 2000 Dalton molecular weight cut-off cellulose membrane against bulk water. The average number of monomer units per polymer of the surfactants used in this study was estimated to be 30–37. These numbers were calculated from average molecular weights as determined by ultracentrifugation. All monomers and polymers used in this study were 99% pure or better, as determined from elemental analysis.

Materials

The (±)1,1'-bi-2-naphthol (BOH); (−)1,1'-bi-2-naphthol; (+)1,1'-bi-2-naphthol; (±)1,1'-bi-2-naphthyl-2,2'-diyl hydrogen phosphate (BNP); (−)1,1'-bi-2-naphthyl-2,2'-diyl hydrogen phosphate; and (+) 1,1'-bi-2-naphthyl-2,2'-diyl hydrogen phosphate were purchased from Aldrich (Milwaukee, Wis.). The tris (hydroxymethyl)aminomethane (TRIS) was purchased from Fisher Scientific Company (Fair Lawn, N.J.). The N-hydroxysuccinimide, undecylenic acid, valine, leucine, valine-valine, leucine-leucine, valine-leucine, and leucine-valine were purchased from Sigma (St. Louis, Mo.). All amino acids and dipeptides used in this study were L-form, except as otherwise noted. These reagents were used as received.

Choice and Preparation of Buffer

The background electrolyte (BGE) for all EKC experiments was 100 mM TRIS, pH 10.5. An appropriate percentage (w/v) of the polymerized surfactants was then added to the BGE, and the pH readjusted with 1 N NaOH or 1 N HCl if necessary. The buffer TRIS was chosen because its low mobility should more closely match that of the analytes chosen, as compared to more conventional buffers such as borate and phosphate. The low mobility of TRIS also allowed higher concentrations of buffer to be used without significantly increasing the current. In addition, a lower current allowed the use of higher voltages, thus yielding shorter retention times. The relatively high ionic strength of the buffer led to sharper, more defined peaks. The pH of 10.5 was chosen because previous work in our laboratory had determined that binaphthyl derivatives are separated best at pH~10. Note that, although TRIS worked well in this system at pH 10.5, TRIS is not normally used at this pH since the pKa of TRIS is around 8; therefore a pH of 10.5 is outside the normal range of its buffering capacity.

Capillary Electrophoresis Procedures

The EKC experiments were conducted on a Hewlett Packard[3D] CE model # G1600AX. An untreated fused silica capillary (effective length 55 cm, 50 µm i.d.) was purchased from Polymicro Technologies (Phoenix, Ariz.). The surfactants were added to the buffer solution, and the solutions were filtered through a 0.45 µm membrane filter. The analytes were prepared in a 50:50 methanol/water mixture at 0.1 mg/mL. The sample was pressure injected for 2 seconds at 25 mbar of pressure. Separations were performed at +30 kV, with UV detection at 215 nm. The temperature of the capillary was maintained at 25° C. by the instrument's thermostat system, which included a peltier element for forced air cooling and temperature control. Prior to use, the new capillary was conditioned for 30 minutes with 1 N NaOH, followed by 30 minutes of 0.1 N NaOH. The capillary was then rinsed for 15 minutes with deionized water. Prior to each run, the buffer was pressure injected through the column for 2 minutes to condition and fill the capillary.

Comparisons of L-SUVL and L-SULV

Separations of BNP and BOH with poly L-SUL V and poly L-SUVL

We compared separations of 1,1'-bi-2-naphthyl-2,2'-diyl hydrogen phosphate (BNP) and 1,1'-bi-2-naphthol (BOH) using the dipeptide surfactants poly L-SULV and poly L-SUVL. In poly L-SULV, valine is the terminal amino acid while it is the first amino acid in poly L-SUVL. The difference between poly L-SULV and poly L-SUVL in chiral recognition of BNP was dramatic. The maximum resolution we achieved with poly L-SUVL was less than 1, while poly L-SULV was able to resolve BNP with a resolution of almost 8 under otherwise identical conditions. The difference in chiral selectivity toward BOH was only slightly less, $R_s$~2.5 for L-SUVL, and $R_s$~6 for L-SULV. Although analyte resolution was dependent on which polymer was used, the optimum polymer concentration for a given analyte appeared to be independent of the polymer. For example, the optimum polymer concentration for BOH was about 0.6% (w/v), and the optimum polymer concentration for BNP was about 3% (w/v).

Comparison of the Monomers and Polymers of L-SUL V and L-SUVL for Separations of BNP and BOH We observed several differences in comparing the separation performance of polymers of L-SUVL and L-SULV to the separation performance of the corresponding monomers. The polymers were considerably better than the monomers at separating BOH. The monomers of L-SULV and L-SUVL showed decreased resolution as the concentration of monomer decreased and approached the CMC (approximately 10 mM, or slightly less than 1% (w/v)). The polymers, on the other hand, showed significantly increased resolution at concentrations below the CMC of the monomers. The optimum resolutions of BOH achieved with the monomers of L-SULV and L-SUVL were $R_s$<2 and $R_s$<1, respectively, while the optimum resolutions with the polymers were $R_s$~6 and $R_s$~3, respectively. The polymers were able to resolve BOH approximately three times better than the monomers. Because the polymers do not have any CMC, they can be effective at concentrations below which the monomeric surfactants do not form micelles, and are thus no longer capable of chiral separations. The importance of this feature is highlighted by examples such as these, where the optimum concentration of polymeric surfactant is below the CMC of the monomer.

In separations of BNP, both the monomer and the polymer of L-SULV produced roughly comparable separations of BNP. However, the L-SUVL monomer provided better separation of BNP than did the polymer. To confirm that this result was not the result of human error, a second batch of L-SUVL polymer was synthesized, which performed in the same manner. The reason for this anomaly is not currently understood. Of all the various chiral polymeric surfactants that our laboratory has studied, this separation is the first instance we have observed in which the monomeric surfactant produced better chiral separation than the corresponding polymer.

Comparison of the Polymers of L-SUL V, L-SUL, and L-SUV

To try to better understand why poly L-SULV gave better separations for BOH and BNP than did poly L-SUVL, we also studied poly L-SUV, and poly (sodium N-undecylenyl-L-leucine) (poly L-SUL). In particular, we examined whether the valine or the leucine might be responsible for the improved chiral resolution, depending on how far the analyte penetrated into the core of the polymerized surfactant. The hypothesis we tested was that if either of these two surfactants (individually) showed comparable chiral resolving power to that of poly L-SULV, then the differences in chiral separations with the dipeptide surfactants might be due to analyte interaction with one of the chiral centers rather than some type of synergism of the two chiral centers. This hypothesis found marginal support in separations of BOH, but failed in separations of BNP.

We found that poly L-SULV was able to separate BOH better than either poly L-SUL or poly L-SUV. While the differences in resolution were not dramatic, Rs~6 for poly L-SULV, $R_s$~4 for poly L-SUL, and Rs~3.5 for poly L-SUV, the differences were significant. However, the differences were not sufficiently significant to draw firm conclusions about whether the observed improvement in chiral separation was due to interaction of the analyte with one of the chiral centers, or to synergism of the two chiral centers on the dipeptide surfactant.

Greater differences were seen in enantioseparation of BNP with poly L-SULV as compared to poly L-SUL and poly L-SUV. The maximum resolution for BNP was less than 1 both for poly L-SUV and for poly L-SUL, while poly L-SULV was able to resolve BNP with a resolution of approximately 8. At faster separation speed, the surfactant poly L-SULV was able to separate BNP in less than six minutes with a resolution of 5.2, at a polymer concentration of 1% (w/v). By contrast, the other surfactants poly (L-SUVL, poly L-SUL, and poly L-SUV) were unable to adequately separate BNP under these conditions. We therefore concluded that the improved chiral separation observed with poly L-SULV was due to some form of synergism between the two chiral centers, or to some type of steric effect of the dipeptide as compared to a single amino acid surfactant.

Comparison of Poly L-SUL V, Poly L-SUV, and Poly L-SULL

To further investigate our working hypothesis that the improved chiral selectivity of poly L-SULV was due to a synergistic effect of the two chiral centers or to steric factors of dipeptide surfactants, we also compared separations with dipeptides of the same amino acids, namely poly (sodium N-undecylenyl-L-leucine-L-leucine) (poly L-SULL), and poly L-SUVV. The polymer of L-SULV performed better than either poly L-SULL or poly L-SUVV in separations of BNP and BOH. Poly L-SULV was able to resolve BOH with a resolution of about 6, while poly L-SUVV and poly L-SULL had resolutions of ~3 and ~2.2, respectively. The resolutions achieved for BNP with the polymers of L-SULV, L-SUVV, and L-SULL were approximately 8, 2, and 4, respectively.

Note that whereas poly L-SUVV better resolved BOH than did poly L-SULL, the opposite was true for BNP. It is also interesting to note that, in comparing the polymers of the dipeptide surfactants L-SULL and L-SUVV to the polymers of the single amino acid surfactants L-SUL and L-SUV, the order of effectiveness of the surfactants in the separation of BNP and BOH followed opposite trends. The bulkier surfactants poly L-SULL and poly L-SUVV separated BNP better than the less bulky, less sterically hindered, single amino acid surfactants. Poly L-SUL and poly L-SUV, however, separated BOH better than the dipeptide surfactants poly L-SULL and poly L-SUVV. The difference was not as great for BOH as for BNP. The separation of BNP appeared to be favored by an increase in steric factors, while the same increase in steric factors decreased the resolution of BOH.

Analysis of our data suggested that two different mechanisms are involved in the interaction of BNP and BOH with the chiral centers of these surfactants. At pH 10.5 (the experimental conditions used), BNP is essentially completely anionic, while BOH is not completely ionized. The first pKa of BOH is about 9.5, so BOH is only partially ionized at pH 10.5. Experiments were also performed at pH 12 (buffered with 50 mM CAPS, +30 kV applied voltage), at which BOH was essentially completely ionized. Although the order of effectiveness of the surfactants for separations of BNP and BOH remained the same at this higher pH, the optimum concentration of surfactant for BOH shifted to higher concentrations. A plot of concentration versus resolution then became similar to that of BNP.

Comparison of Optimum Resolutions, and k' at Optimum Resolution for the Various Polymeric Surfactants Poly L-SULV was clearly the best surfactant tested for separating BNP and BOH. The other surfactants used in this study showed different results for these two compounds. Poly L-SULV and poly L-SULL provided better separations of BNP than of BOH. The other surfactants, poly L-SUVV, poly L-SUVL, poly L-SUL and poly L-SUV separated BOH better than BNP. Furthermore, as the resolution of BNP separations decreased, there was a relative increase in the resolution of BOH separations—with the exception of poly L-SULV, which separated both compounds better than any of the other surfactants examined. The ratios of (resolution of BNP: resolution of BOH) decreased in the following order: poly L-SULL>poly L-SUVV>poly L-SUVL>poly L-SUV>poly L-SUL. This trend is consistent with our hypothesis that two different mechanisms are involved in the interaction of BNP and BOH with the chiral centers of these surfactants.

One possible reason for the observed improvements in the selectivity of the chiral analytes could be differences in the binding of the analytes BNP and BOH to the various surfactants. The major factors in the binding of these analytes to the surfactants used in this study are hydrophobic-hydrophilic interactions, hydrogen bonding, and steric factors. The steric factors include elements such as the size of the R-group attached to the chiral carbon of the amino acid, and the configuration of the surfactant in solution. Configurational differences of the surfactants could either increase or decrease the flexibility of the surfactant core, or increase or decrease hydrogen bonding of the analyte to the surfactant.

To determine whether a difference in binding was responsible for the observed differences in chiral selectivity, the "optimum" capacity factors (k') of the polymers were compared. The "optimum" k' values were defined as the k' values at the concentration of surfactant that yielded optimum resolution. The optimum concentration of surfactant was approximately 3% (w/v) for BNP, and about 0.6% (w/v) for BOH. The optimum k' values were found to be approximately the same for all surfactants that gave adequate separation of analyte. The three surfactants that did not adequately resolve BNP were poly L-SUVL, poly L-SUL, and poly L-SUV. The k' values for these three surfactants were significantly higher than the k' values of the three surfactants (poly L-SULV, poly L-SULL, and poly L-SUVV) that did adequately resolve BNP. The average optimum k' values for the surfactants that yielded adequate separation was approximately the same, within experimental error, for both analytes, 1.3±0.1 for BNP and 1.1±0.2 for BOH.

The increased k' values for the surfactants that did not adequately resolve BNP support the hypothesis that an increase in steric factors is responsible for the improvement in resolution of BNP. BNP bound more strongly to these surfactants than to the surfactants that adequately resolved BNP. Since all surfactants studied had approximately the same number of carbon atoms, the hydrophobicity of the surfactant core may be assumed to be approximately the same for all the dipeptide surfactants. Furthermore, since the number of heteroatoms available for hydrogen bonding was the same for all the dipeptide surfactants, the major difference in binding is believed to be due to steric factors that either block the analyte from entering the core of the surfactant, or increase binding to the surfactant core, or increase the flexibility of the surfactant core. Since it is assumed that hydrophobic-hydrophilic interactions with all dipeptide surfactants were approximately the same, we concluded that the differences in binding must be primarily due to steric factors.

The high selectivity of poly L-SULV allowed baseline separations of BNP and BOH in less than one minute, using 1% (w/v) polymer with reverse polarity, and injecting the sample at the detector end, making the effective length of the capillary only 8.5 cm. These separations were initially performed with enantiomeric excess of the R-forms of BOH and BNP to determine the elution order of the enantiomers. This ultra-fast separation allows higher sample throughput, which is particularly important for increased laboratory efficiency when used for analytical purposes, and for lower costs of production when used for preparative purposes. Such separations are not possible under similar conditions with the monomer since the CMC is about 1% (w/v), and the separation of BOH and BNP drop off rapidly as the CMC is approached.

A systematic study is presently under way in which all possible combinations of the L-form of the three amino acids alanine (A), valine (V), and leucine (L) in dipeptide surfactants are evaluated. Examination of the dipeptides from the nine possible combinations of these amino acids (A—A, A–V, A–L, V–A, V—V, V–L, L–A, L–V, and L—L) should aid in an understanding of the role of amino acid order in dipeptide surfactants for chiral recognition.

In addition, we have made polymerized surfactants from all possible dipeptide combinations of glycine (which lacks a chiral center) and the L-forms of alanine, valine, and leucine. The enantioselectivity of these surfactants was compared with thirteen different chiral analytes. We found, for example, that SUL-Gly worked as well as SULV for the separation of BNP, but SUL-Gly worked better for BOH than did SULV.

Using automated techniques, a worker of ordinary skill in the art could routinely evaluate all possible 400 dipeptides of the 20 "standard" L-form amino acids, to determine which polymerized dipeptide surfactant affords the best separation for a given pair of enantiomers.

Naturally occurring or xenobiotic amino acids other than the 20 "standard" amino acids may also be used in practicing the present invention. D-form amino acids may also be used, either alone or in combination with L-form amino acids. For the reasons discussed in the following section, results will generally be better when all amino acids in the surfactant have the same configuration, i.e., all L-form or all D-form.

III. Determination of Chiral Separation Mechanisms

Without wishing to be bound by this theory, we propose a mechanism underlying chiral separations with polymerized dipeptide surfactants. In particular, we propose that one of the primary factors that determines chiral selectivity of the analyte with polymerized dipeptide surfactants is the depth to which the analyte penetrates into the core of the surfactant. The depth of penetration determines the chiral center, or centers, with which the analyte preferentially interacts. Hydrophobic interactions are important to the chiral recognition of some chiral molecules. One may readily determine the importance of hydrophobic and electrostatic interactions for a given analyte.

We examined five analytes with differing hydrophobicity and charge states, and eight polymerized surfactants. The primary surfactants were poly sodium N-undecyl (L-L)-leucine-leucine (poly (L-L)-SULL), poly sodium N-undecyl (D-D)-leucine-leucine (poly (D-D)-SULL), poly sodium N-undecyl (L-D)-leucine-leucine (poly (L-D)-SULL), poly sodium N-undecyl (D-L)-leucine-leucine (poly (D-L)-SULL), poly sodium N-undecyl D-leucine (poly D-SUL), and poly sodium N-undecyl L-leucine (poly L-SUL). To gain additional insights into the separation mechanisms, two other dipeptide surfactants containing only one chiral center were also used, poly sodium N-undecyl L-leucine-glycine (poly L-SULG) and poly sodium N-undecyl L-glycine-leucine (poly L-SUGL). Glycine, an achiral amino acid, serves as a "spacer" for placing a chiral amino acid as the C-terminal or N-terminal amino acid with a given dipeptide surfactant. Enantiomeric separations were performed with these surfactants on two cationic β-blockers, propranolol (Prop) and alprenolol (Alp); as well as on three model atropisomers, (±)1,1'-bi-2-naphthol (BOH), (±)1,1'-bi-2-naphthyl-2,2'-diamine (BNA) and (±)1,1'-bi-2-naphthyl-2,2'-diyl hydrogen phosphate (BNP).

Synthesis of Polymerized Surfactants

All surfactants in this study were synthesized using the procedures described above. All polymers studied were found to be 99% pure or better, as estimated from elemental analysis.

Materials

The racemic mixtures and the pure optical isomers of 1,1'-bi-2-naphthol (BOH), 1,1'-bi-2-naphthyl-2,2'-diamine (BNA), 1,1'-bi-2-naphthyl-2,2'-diyl hydrogen phosphate (BNP), propranolol (Prop), and alprenolol (Alp) were purchased from Aldrich (Milwaukee, Wis.). The 3-(cyclohexylamino)-1-propanesulfonic acid (CAPS), and sodium borate were obtained from Fisher Scientific Company (Fair Lawn, N.J.). Chemicals used for the synthesis of surfactants included: N,N'-dicyclohexylcarbodiimide (DCC), N-hydroxysuccinimide, undecylenic acid, various amino acids and the dipeptides, and were obtained from Sigma (St. Louis, Mo.) and used as received.

Preparation of EKC Buffer Solutions

The background electrolyte (BGE) for separation of the binaphthyl derivatives was 50 mM sodium borate at pH 10.0. The BGE used for the cationic β-blockers was 50 mM sodium borate and 300 mM CAPS at pH 8.5. CAPS was added to minimize capillary wall interaction. The appropriate percentage (w/v) of the polymerized surfactant was then added to the BGE, and the pH was readjusted with 1 M NaOH or 1 M HCl if necessary.

Capillary Electrophoresis

The EKC experiments were conducted on a Hewlett Packard 3D CE model # G1600AX. An untreated fused silica capillary (effective length 55 cm, 50 μm i.d.) was purchased from Polymicro Technologies (Phoenix, Ariz.). The surfactants were added to the buffer solution, and the solution was filtered through a 0.45 mm membrane filter. Separations were performed at +30 kV, with UV detection at 215 nm. The temperature of the capillary was maintained at 25° C. for the binaphthyl derivatives, and at 12° C. for Prop and Alp with the instrument's thermostat system, which comprised a Peltier element for forced air cooling and temperature control. The binaphthyl derivatives (BNP, BNA, and BOH) were prepared in 50:50 methanol:water at 0.1 mg/mL. Propranolol and Alp were prepared in 50:50 methanol:water at a concentration of 2.5 mg/mL. The samples were injected for 5 seconds with 10 mbar of pressure. Prior to use, the new capillary was conditioned for 30 minutes with 1 M NaOH, and then for 30 minutes with 0.1 M NaOH. Finally, the capillary was rinsed for 15 minutes with triply distilled deionized water. Prior to each run, the capillary was flushed with the EKC buffer for 2 minutes to condition and fill the capillary.

Proposed Interactions

Figure 6:
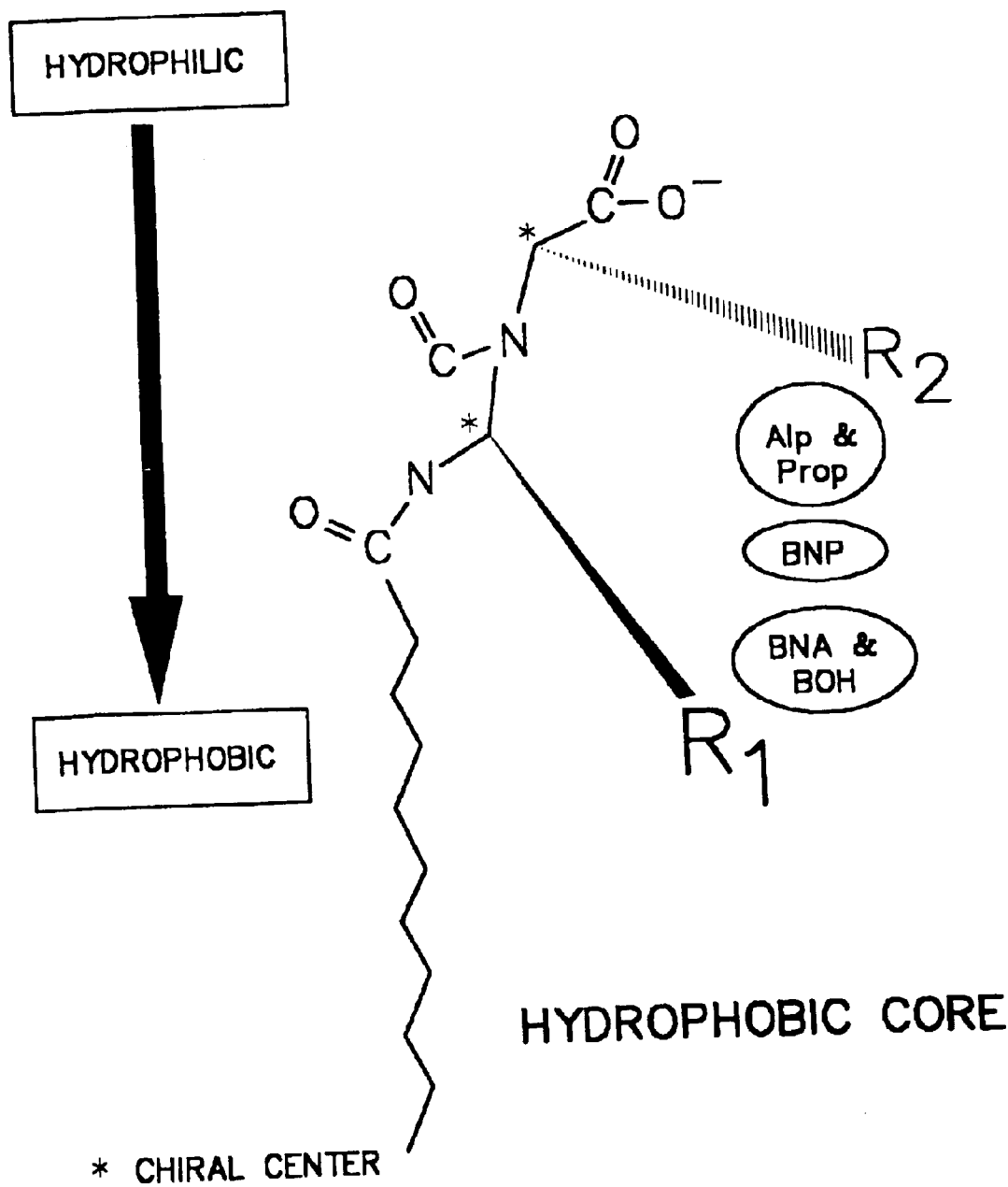
FIG. 6 depicts a schematic illustration of the proposed interactions involved in the chiral separations.

Initial studies with our polymerized dipeptide surfactants suggested that one of the factors determining chiral selectivity for those surfactants is the depth to which the analyte penetrates into the hydrophobic core of the polymerized surfactant. We postulate that the hydrophobicity and charge interactions of the analyte with the surfactant determine the depth to which the analyte will penetrate into the hydrophobic core of the surfactant. A schematic illustration of the proposed interactions is depicted in FIG. 6. In this figure, $R_1$ represents the side chain attached to the first amino acid (the N-terminal or innermost amino acid), and $R_2$ is the side chain attached to the second amino acid (the C-terminal or outermost amino acid). The first amino acid is in a more hydrophobic region (further from the bulk aqueous phase) of the polymerized dipeptide surfactant core than is the second amino acid. We propose that the more hydrophobic the chiral analyte, the more it will tend to shield itself from the bulk aqueous phase. Hence, more hydrophobic analytes will tend to penetrate deeper into the core than will less hydrophobic chiral analytes.

The depth to which the analyte penetrates into the core of the micelle determines the portion of the polar head group with which the analyte preferentially interacts. If the analyte penetrates deep into the core, it will interact predominantly with the first chiral center, attached to $R_1$. If the analyte is more hydrophilic or cationic, it will interact more with $R_2$, which is closer to the bulk aqueous phase than $R_1$. If the analyte is only moderately hydrophobic, it may interact with both chiral centers more-or-less equally, and its separation will thus be dependent on the configuration of both amino acids. One would expect little or no chiral separation for an analyte of moderate hydrophobicity that interacts with both chiral centers, if those chiral centers have opposite optical configurations.

Enantiomeric Separation of Alprenolol and Propranolol

Because the dipeptide surfactants used in this study were anionic, electrostatic repulsion should be one of the major factors governing the interaction (and thus the chiral recognition) of anionic species with the polymerized dipeptide surfactants. The first set of analytes (Alp and Prop) tested in this study were cationic under the EKC conditions used here, and in accordance with the above hypothesis were therefore expected to preferentially bind to the outside, C-terminal amino acid.

As predicted, the two cationic analytes were found to bind primarily to the outside (C-terminal) amino acid. Evidence of this binding is seen in the elution order of the enantiomers of Alp and Prop with the single amino acid surfactants of opposite optical configuration, poly L-SUL and poly D-SUL. The (+) form of both Alp and Prop, which was present at half the concentration of the (−) form, eluted first for poly D-SUL. As expected, when poly D-SUL was replaced with poly L-SUL, the order of elution was reversed. A comparison of dipeptide surfactants with the same optical configuration at both chiral centers, in particular poly (L—L)-SULL and its antipode poly (D—D)-SULL, showed the same relative elution orders as had been seen with the single amino acid surfactants, with the same reversal of enantiomeric order upon switching from L—L to D—D. The order of elution of the enantiomers was the same for poly D-SUL, poly (D—D) SULL and poly (L–D) SULL, i.e., the (+) form of both Alp and Prop always eluted first. The (+) form eluted second in the case of poly L-SUL, poly (L—L) SULL and poly (D–L) SULL. These elution orders suggest that chiral recognition for Alp and Prop occurs primarily at the C-terminal amino acid (outermost amino acid) of the polymerized dipeptide surfactants.

Further evidence of the preferential interaction of Alp and Prop with the outermost C-terminal amino acid was seen in a comparison of the resolution of the enantiomers of Alp and Prop with dipeptide surfactants containing only one chiral center (poly L-SULG and poly L-SUGL). Poly L-SUGL produced baseline resolution of the enantiomers of both Alp and Prop. By contrast, poly L-SULG provided no enantiomeric separation for Alp, and only slightly resolved the enantiomers of the more hydrophobic analyte Prop.

Enantiomeric Separation of Binaphthyl Derivatives

The role of hydrophobicity was further examined in separations of the binaphthyl derivatives. The EKC data for the binaphthyl derivatives suggested that BOH and BNA bind primarily to the inside, N-terminal amino acid. Conversely, we predict that BNP, which is anionic and thus less hydrophobic than BOH or BNA, will not penetrate as deeply into the core of the polymerized surfactant, and that it may bind with both chiral centers ($R_1$ and $R_2$).

As before, the single amino acid surfactants poly L-SUL and poly D-SUL were examined to determine the elution order of the enantiomers of BNP, BOH, and BNA. The most hydrophobic of the three is BNA, which was neutral under the experimental conditions (50 mM sodium borate, pH 10); BOH was partially ionized ($pKa_1 \sim 9.5$); and BNP was completely anionic. The S-form of BNA, which was present at half the concentration of the R-form, eluted first with poly L-SUL. As expected, when poly L-SUL was replaced with poly D-SUL, the order of elution of the BNA enantiomers was reversed.

Evidence of the preferred site of interaction for BOH and BNA was seen in the elution order of the enantiomers with the various dipeptide surfactants. A comparison of dipeptide surfactants with the same optical configuration at both chiral centers, poly (L—L)-SULL and its antipode poly (D—D)-SULL, showed the expected reversal of enantiomeric order for BNA; with the relative order of elution the same as for the corresponding poly L-SUL or poly D-SUL. Evidence of the chiral interaction of BNA with the inside, N-terminal amino acid was seen in a comparison of poly L-SUL, poly (L—L)-SULL, and poly (L–D)-SULL: The R-form eluted second in each of these three cases. In the case of poly D-SUL, poly (D—D)-SULL, and poly (D–L)-SULL, the R-form eluted first. These results indicated that chiral recognition of BNA occurred primarily at the inside (N-terminal) amino acid ($R_1$ of FIG. 6).

Similar results were observed for BOH. The R-form of BOH eluted second for poly L-SUL, poly (L—L)-SULL and poly (L–D) SULL; while it eluted first for poly D-SUL, poly (D—D) SULL, and poly (D–L) SULL.

Although these results led us to conclude that chiral recognition for BOH and BNA occurred primarily at the inside (N-terminal) amino acid, these compounds also interact to some extent with the outside (C-terminal) amino acid. This secondary interaction is evidenced by the observed decrease in chiral resolution of BOH and BNA for the D–L and L–D configurations as compared to the D—D and L—L configurations of poly SULL. In each case, the enantioseparation was approximately the same for the D-form as compared to the L-form; for the L—L form as compared to the D—D form; and for the L–D form as compared to the D–L form. However, a comparison of dipeptide surfactants with the same optical configurations (i.e., L—L, D—D) versus the dipeptide surfactants with different optical configurations (i.e., L–D, D–L) showed a marked decrease in chiral resolution of both BNA and BOH with the dipeptides having different optical configurations (i.e., L–D, D–L). Because the chiral selectivities of the D and L forms are opposite, interaction of an analyte with two chiral centers of opposite configuration tends to reduce chiral selectivity. BNA is neutral, and BOH is only partially anionic under the conditions used, so both are more hydrophobic than BNP, which was essentially completely ionized. We expected different trends for BNP as compared to BOH and BNA due to its greater hydrophilicity.

The data for BNP support the conclusion that BNP did not penetrate as deeply into the hydrophobic core of the polymerized surfactant as did BOH and BNA. The elution order was the same for poly L-SUL and poly (L,L) SULL (R first, S second), while the opposite elution order was observed for poly D-SUL and poly (D,D) SULL, (S first, R second). By contrast to the results for BOH and BNA, no resolution of enantiomers was seen for BNP with poly (L,D)-SULL or poly (D,L)-SULL. A possible explanation is that since BNP is anionic at pH 10, it should not penetrate as deeply into the core of the polymerized surfactant as the neutral, more hydrophobic binaphthyl derivatives (BOH and BNA). Thus, another factor that may play a role in determining the preferential site of interaction for BNP is electrostatic repulsion. However, in either case it appeared that BNP interacted with both chiral centers, since no chiral separation was observed for with poly (L,D)-SULL or poly (D,L)-SULL. In contrast, poly (L,L)-SULL and poly (D,D)-SULL separated the enantiomers of BNP very well. Since BNP should not penetrate as deeply into the core, we postulate that it interacted with both chiral centers (D and L). It is reasonable to assume that if an analyte interacts approximately equally with two chiral centers of equal chiral selectivity but opposite configuration, then essentially no enantiomeric resolution should result.

Further evidence for the preferred interaction sites of BOH, BNA, and BNP can be seen in experiments using the single chiral center dipeptide surfactants poly L-SULG and poly L-SUGL. The achiral amino acid glycine served as a "spacer" for placing the chiral amino acid as the C-terminal or N-terminal amino acid in a dipeptide surfactant. No chiral recognition was observed for BOH or for BNA with poly L-SUGL, while poly L-SULG separated both BOH and BNA very well. These observations further support our working hypothesis that BOH and BNA bind primarily with the N-terminal amino acid. We proposed above that, since no chiral separation was observed for BNP with the polymerized dipeptide surfactants of opposite optical configuration, poly (L,D) SULL and poly (D,L) SULL, then BNP interacted with both chiral centers on the dipeptide surfactant. The results from the single chiral center dipeptide surfactant study are in agreement with this hypothesis. Both poly L-SULG and poly L-SUGL provided excellent resolution of BNP. These results suggested that BNP did not penetrate as deeply into the core as did BOH and BNA, since poly L-SUGL was able to separate BNP but not BOH or BNA.

Finally, in comparing the migration times of the enantiomers of BOH, BNA, and BNP for poly (L,L) SULL and poly (D,D) SULL, an interesting trend was observed. Although the elution order reversed as expected, it appeared that the elution time of the R (+) enantiomers for BOH and BNA was not affected by the optical configuration of the dipeptide surfactants. By contrast, the elution time of the S (-) enantiomers of BNA and BOH changed by about 0.7 and 1.2 minutes, respectively, thereby reversing the overall elution order. The same behavior was observed for enantiomers of BNP for poly (L,L) SULL and poly (D,D) SULL. The elution time for the S (+) enantiomer was approximately the same for both surfactants, while the elution time of the R (-) enantiomer changed by about 0.6 minutes. Intuitively, one would have expected the elution order and the retention times of the enantiomers simply to reverse, as was observed for the single amino acid surfactants of poly L-SUL and poly D-SUL. Since the elution time of the (+) enantiomers was unaffected by the change in optical configuration for the dipeptide surfactants poly (L,L) SULL and poly (D,D) SULL, it seems reasonable to believe the stability of the diastereomeric complexes for the (+) enantiomers of these dipeptide surfactants was essentially the same. By contrast, the change in the retention times of the (-) enantiomers indicated that the diastereomeric complexes formed for poly (L,L) SULL and poly (D,D) SULL were not equivalent, for reasons that are not presently understood.

Summary

The results of this set of studies suggests that one of the major factors determining chiral resolutions with polymerized dipeptide surfactants is the depth to which the analyte penetrates into the hydrophobic core of the surfactant. The depth of penetration of the analyte is governed by two major factors: the hydrophobicity of the analyte, and electrostatic interactions. The more hydrophobic the analyte (e.g. BOH and BNA), the more it interacts with the inside (N-terminal) amino acid on the polar head group of the polymerized dipeptide surfactant. Thus, chiral selectivity is governed primarily by the innermost amino acid. Conversely, if the analyte is relatively hydrophilic and/or cationic (e.g. Prop, Alp), it interacts primarily with the outside C-terminal amino acid. However, if the analyte is moderately hydrophobic (e.g. BNP), it may interact with both chiral centers on the polymerized dipeptide surfactant, and its chiral selectivity will thus depend on the optical configuration of both chiral centers. It should be kept in mind that, although enantiomers may interact primarily with one of the chiral centers on a dipeptide surfactant, the interaction is not necessarily limited to that one chiral center. Analytes may interact with both chiral centers. In general, dipeptide or oligopeptide surfactants are more effective when all chiral centers have the same chirality; e.g., all L-form amino acids or all D-form amino acids, but not mixtures of L- and D-form amino acids.

Dipeptide chiral micelle polymers in accordance with the present invention may be used as mobile phase additives for chiral separations in capillary electrophoresis, or in micellar liquid chromatography under reversed phase conditions. Our method of preparing chiral micelle polymers is easy to implement, and readily lends itself to use with a variety of polymers having different structures and degrees of chirality, which can be manipulated to enhance the chiral separations for particular analytes. Using synthetic means known in the art, the chiral centers can be moved to different locations along the individual monomers, and the number of chiral centers per micelle can be increased or decreased by using micelles with higher or lower aggregation numbers, respectively. Different monomer lengths may readily be generated through means known in the art. Fatty acid-type monomers terminating in double bonds are preferred, because such monomers may be used in the synthetic scheme described above with minimal modifications to the synthesis.

Different, or mixed polymerized chiral micelles could be used in a separation, which can result in enhanced separation where the different micelles have complementary separation properties. For example, a poly (sodium N-undecylenyl valine valine) micelle could be placed in solution with a poly (sodium N-undecylenyl phenylalanine phenylalanine) to take advantage of the different properties of their different resolving properties.

Alternatively, different chiral surfactant monomers may be copolymerized. Copolymers frequently have properties differing from those of either corresponding homopolymer. For example, a surfactant monomer incorporating two L-valines could be combined with one incorporating two L-phenylalanines to form a mixed micelle; or both amino acids could be incorporated into the dipeptide monomer. A polymerized micelle formed from this system would have chiral recognition properties similar to those of poly (L-SUVV), in addition to the π-interaction chiral recognition properties of phenylalanine.

The synthetic scheme outlined above is a fairly general one in which the final steps may be modified to obtain a surfactant monomer with a different chiral center. For example, if π—π interaction is desired at the chiral center, phenylalanine, tyrosine, or tryptophan could be used in place of valine in the monomer synthesis. Histidine could also be used where a π—π interaction is desired, with care taken to "protect" one of the two amino groups of the histidine ring during synthesis.

In general, any unsaturated fatty acid may be substituted for undecylenic acid to serve as the "backbone" for the chiral monomer. Examples of naturally-occurring, readily available unsaturated fatty acids include palmitoleic acid, oleic acid, linoleic acid, linolenic acid, arachidonic acid, caproleic acid, elaidic acid, brassidic acid, erucic acid, nervonic acid, and vaccenic acid. The chemistry of attaching the chiral group to these unsaturated fatty acids, and their polymerization into chiral micelle polymers, will be essentially similar to that described above. Although preferred, the "backbone" of the monomer need not be a fatty acid or fatty acid derivative. Other amphophilic molecules could also be used for the "backbone," using methods known in the art of organic synthesis for attaching chiral groups to the backbone, and for polymerizing the chiral surfactant monomers into micelle polymers.

An example of the present invention is a polymerized dipeptide chiral micelle; wherein said polymerized dipeptide chiral micelle is not a polymer of a compound selected from the group consisting of N-undec-10'-enoyl-L-prolyl-L-glutamic acid, N-undec-10'-enoyl-L-methionyl-L-gl utamic acid, and N-undec-10'-enoyl-L-phenylalanyl-β-alanine. Another example of the present invention is a polymerized dipeptide chiral micelle as just described, wherein said micelle comprises a polymer of monomers, wherein each of said monomers comprises an unsaturated hydrocarbon chain linked to a chiral dipeptide.

Various amino acids can be substituted for valine to synthesize other surfactant monomers analogous to L-SUVV, surfactant monomers that can then be polymerized to form other micelle polymers. Any amino acids may be used as the chiral groups, including alanine, valine, leucine, isoleucine, proline, tryptophan, phenylalanine, methionine, glycine, serine, threonine, tyrosine, cysteine, glutamine, asparagine, lysine, arginine, histidine, aspartic acid, glutamic acid, and modified amino acids.

In addition to γ-cyclodextrin, where desired other chiral selectors known in the art may be used to enhance the chiral separations obtained with the chiral micelle polymers. For example, the smaller α- or β-cyclodextrins could be advantageously used where a smaller analyte is being separated. Other water-soluble cyclodextrin compounds that may be used for this function include cyclodextrin polymers, carboxylic acid derivatives of a cyclodextrin, and hydroxypropyl- and hydroxyethyl- derivatives of α-, β-, and γ-cyclodextrins. Non-cyclodextrin chiral selectors may also be used as enhancers, including chiral crown ethers and bile salts.

Dipeptide chiral micelle polymers in accordance with the present invention may also be used in liquid chromatography, for example as part of the mobile phase in a reversed-phase system employing a C-18 column. Especially in chromatographic systems, dipeptide chiral micelle polymers in accordance with the present invention may be used on a preparative scale to purify large quantities of racemic mixtures. An additional advantage to using polymerized chiral micelles in liquid chromatography is that column back pressure should be reduced. In liquid chromatography with "conventional" micelles, chromatographic efficiency can be reduced due to high column back pressure attributable to coating of the stationary phase with surfactant monomers. Such coating should not occur with the polymerized micelles, because unpolymerized monomers are essentially absent.

Polymerized dipeptide chiral micelles in accordance with the present invention could be used in otherwise-conventional liquid-liquid extraction systems, in which the polymerized chiral micelle is soluble only in one of the liquid phases. For example, poly (L-SUVV) could be used in an aqueous phase extraction of a chiral compound that is soluble in an organic phase such as chloroform.

Polymerized chiral micelles in accordance with the present invention could also be used in a selective extraction medium or liquid membrane transport system, in which a polymerized chiral micelle preferentially transports one enantiomer across a membrane. For example, a membrane system could be constructed from a three-phase system comprising an aqueous phase containing a chiral micelle polymer and two organic phases, in which each of the three phases is immiscible in the other two, and in which the aqueous phase is intermediate in density between the two organic phases. The aqueous phase with the chiral micelle polymer acts as a transport membrane between the two organic phases. A racemic mixture dissolved in one of the organic phases could be resolved by selective transport through the aqueous membrane into the other organic phase.

Polymerized dipeptide chiral micelles in accordance with the present invention could also be used in micelle-enhanced ultrafiltration. In this technique, micelles are added to an aqueous phase containing a racemic mixture. The aqueous mixture is then passed through an ultrafiltration membrane whose pore size is small enough to prevent micelles from passing through. The enantiomer with the higher affinity for the polymerized chiral micelle is enriched in the retainant, and the solution passing through the filter is enriched in the other enantiomer.

The present inventions will work not only with "normal" polymerized chiral micelles, but also with "reversed" polymerized chiral micelles. In a "normal" micelle in an aqueous or other polar solvent, the hydrophilic portions of the surfactant molecules are on the outside of the micelle, interacting with the polar solvent, while the hydrophobic portions of the surfactant molecules are on the inside of the micelle to form a nonpolar, pseudo-stationary phase. By contrast, in a "reversed" micelle in a nonpolar solvent, the hydrophobic portions of the surfactant molecules are on the outside of the micelle, interacting with the nonpolar solvent, while the hydrophilic portions of the surfactant molecules are on the inside of the micelle to form a polar, pseudo-stationary phase. The interior of a reversed micelle typically contains a small amount of a polar solvent such as water. Conventional "reversed" micelles are well known in the art. "Reversed" polymerized chiral micelles will be useful in performing chiral separations. For example, poly (sodium N-undecylenyl-L-valine-L-valine) and poly (sodium N-undecylenyl-D-valine-D-valine) can also be used as "reversed" polymerized chiral micelles. When used as reversed micelles, the surfactant monomers will be synthesized in a minimum amount of water, and the polymerization will be performed in a nonpolar organic solvent such as cyclohexane. It should also be noted that the chiral center(s) need not be located in the hydrophilic portion of the surfactant, but may be in the hydrophobic portion of the molecules.

In chromatographic applications, polymerized chiral micelles in accordance with the present invention may be present in the mobile phase, or they could instead be incorporated into chiral stationary phases such as gels, wall coatings, and pack capillaries through means known in the art. For example, a gas chromatography capillary column may be packed with silica particles that have been coated with polymerized chiral micelles. Another possibility is the combination of a chiral mobile phase incorporating polymerized chiral micelles in accordance with the present invention, with a different chiral stationary phase. This combination can result in separation efficiencies that are greater than the sum of the parts.

Where a particular set of conditions results in the separation of two enantiomers, then the same or similar conditions should, in general, also successfully separate homologues of those enantiomers, as well as other enantiomers with similar structures.

While most of the examples tested to date have been polymerized dipeptide surfactants, more generally polymerized oligopeptide surfactants will also give superior results over polymers of single amino acid surfactants. Particularly when using tripeptide- and larger oligopeptide surfactants, it is important to maintain solubility of the polymerized oligopeptide surfactant in the solvent used. For example, when water is the solvent, at least some of the amino acids in the oligopeptide surfactant should be hydrophilic.

Miscellaneous

The complete disclosures of all references cited in this specification are hereby incorporated by reference; as are the complete disclosures of the following papers (none of which are prior art to the present application): Shamsi, S. et al., Anal. Chem. 1997, 69, 2980–2987 (abstract published in Advance ACS Abstracts, Jun. 15, 1997); Billiot, E. et at., Anal. Chem. 1998, 70, 1375–1381; Shamsi, S. et al., "Comparison of Single Amino Acids versus Dipeptide Polymerized Surfactants for Chiral Separations in Electrokinetic Chromatography," Abstract No. 1008 from Pittcon '98 (New Orleans, La., Mar. 1–5, 1998); and Billiot, E. et al., "Effect of Amino Acid Order on Chiral Separations in Dipeptide Surfactants," Abstract No. 1010 from Pittcon '98 (New Orleans, La., Mar. 1–5, 1998).

We claim:

1. A compound selected from the group consisting of sodium N-undecylenyl-L-valine-L-valine; sodium N-undecylenyt-D-valine-D-valine; sodium N-undecylenyl-L-leucine-L-leucine; sodium N-undecylenyl-D-leucine-D- leucine; sodium N-undecylenyl-L-Ieucine-L-valine; sodium N-undecylenyl-D-leucine-D-valine; sodium N-undecylenyl-L-valine-L-leucine; and sodium N-u ndecylenyl-D-valine-D-leucine.

2. A compound as recited in claim 1, wherein said compound is sodium N-undecylenyl-L-valine-L-valine.

3. A compound as recited in claim 1, wherein said compound is sodium N-undecytenyl-D-valine-D-valine.

4. A compound as recited in claim 1, wherein said compound is sodium N-undecylenyl-L-leucine-L-leucine.

5. A compound as recited in claim 1, wherein said compound is sodium N-undecylenyl-D-leucine-D-leucine.

6. A compound as recited in claim 1, wherein said compound is sodium N-undecylenyl-L-leucine-L-valine.

7. A compound as recited in claim 1, wherein said compound is sodium N-undecytenyl-D-leucine-D-valine.

8. A compound as recited in claim 1, wherein said compound is sodium N-u ndecylenyl-L-valine-L-leucine.

9. A compound as recited in claim 1, wherein said compound is sodium N-undecylenyl-D-valine-D-leucine.

10. A polymerized dipeptide chiral micelle, wherein said micelle comprises poly (sodium N-undecylenyl-L-valine-L-valine), or poly (sodium N-undecylenyl-D-valine-D-valine), or poly (sodium N-undecylenyl-L-leucine-L-leucine), or poly (sodium N-undecylenyl-D-leucine-D-leucine), or poly (sodium N-undecylenyl-L-leucine-L-valine), or poly (sodium N-undecylenyl-D-leucine-D-valine), or poly (sodium N-undecylenyl-L-valine-L-leucine), or poly (sodium N-undecylenyl-D-valine-D-leucine).

\* \* \* \* \*